(12) United States Patent
Roberts et al.

(10) Patent No.: US 7,951,812 B2
(45) Date of Patent: May 31, 2011

(54) SUBSTITUTED PYRROLO[2,3-D]PYRIMIDINES AS ANTIFOLATES

(75) Inventors: Michael J. Roberts, Charlotte, NC (US); Simon Pedder, Fort Mill, SC (US)

(73) Assignee: Chelsea Therapeutics, Inc., Charlotte, NC (US)

( * ) Notice: Subject to any disclaimer, the term of this patent is extended or adjusted under 35 U.S.C. 154(b) by 692 days.

(21) Appl. No.: 12/016,528

(22) Filed: Jan. 18, 2008

(65) Prior Publication Data

US 2008/0214585 A1    Sep. 4, 2008

Related U.S. Application Data

(60) Provisional application No. 60/885,719, filed on Jan. 19, 2007.

(51) Int. Cl.
| | |
|---|---|
| C07D 487/04 | (2006.01) |
| A61K 31/519 | (2006.01) |
| A61P 35/00 | (2006.01) |
| A61P 29/00 | (2006.01) |
| A61P 11/06 | (2006.01) |
| A61P 19/02 | (2006.01) |

(52) U.S. Cl. .................................. 514/265.1; 544/278

(58) Field of Classification Search .................. 544/280; 514/265.1

See application file for complete search history.

(56) References Cited

U.S. PATENT DOCUMENTS

| | | | |
|---|---|---|---|
| 4,818,753 | A | 4/1989 | Colwell et al. |
| 4,996,206 | A | 2/1991 | Taylor et al. |
| 4,996,207 | A | 2/1991 | Nair et al. |
| 5,028,608 | A | 7/1991 | Taylor et al. |
| 5,073,554 | A | 12/1991 | Nair |
| 5,106,974 | A | 4/1992 | Akimoto et al. |
| 5,248,775 | A | 9/1993 | Taylor et al. |
| 5,344,932 | A | 9/1994 | Taylor |
| 5,550,128 | A | 8/1996 | Nair et al. |
| 5,593,999 | A | 1/1997 | Nair et al. |
| 5,912,251 | A | 6/1999 | Nair |
| 6,667,318 | B2 | 12/2003 | Burdick et al. |
| 7,060,825 | B2 | 6/2006 | Wu et al. |
| 2002/0081455 | A1 | 6/2002 | Lee |
| 2003/0181635 | A1 | 9/2003 | Kochat et al. |
| 2006/0111272 | A1 | 5/2006 | Roberts et al. |
| 2006/0160751 | A1 | 7/2006 | McGuire |

FOREIGN PATENT DOCUMENTS

| | | |
|---|---|---|
| EP | 0 239 362 | 9/1987 |
| EP | 0 340 905 | 11/1989 |
| WO | WO 93/13079 | 7/1993 |
| WO | WO 02/081455 A1 | 10/2002 |

OTHER PUBLICATIONS

Gangjee et al., "Effect of N-9-Methylation and Bridge Atom Variation on the Activity of 5-Substituted 2, 4-Diaminopyrrolo (2,3-d) Pyrimidines Against Dihydrofolate Reductases From *Pneumocystis carinii* and *Toxoplasma gondii*," *Journal of Medicinal Chemistry*, 1997, pp. 1173-1177, vol. 40, No. 7.

Itoh et al., "Non-Glutamate Type Pyrrolo[2,2-d]pyrimidine Antifolates. II. Synthesis and Antitumor Activity of N-Substituted Glutamine Analogs," *Chemical and Pharmaceutical Bulletin, Pharmaceutical Society of Japan*, 1996, pp. 1498-1509, vol. 44, No. 8.

Miwa et al., "A Novel Synthetic Approach to Pyrrolo(2,3-d)pyrimidine Antifolates," *Journal of Organic Chemistry*, 1993, pp. 1696-1701, vol. 58, No. 7.

McGuire, et al., "Metabolism-blocked Antifolates as Potential Antirheumatoid Arthritis Agents: 4-Amino-4-deoxy-5,8,10-trideazapteroyl -D,L-4'-methyleneglutamic Acid (CH-1504) and Its Analogs," *Biochemical Pharmacology*, 2009, pp. 1161-1172, vol. 77, No. 7.

Abraham et al., "Folate Analogues. 34. Synthesis and Antitumor Activity of Non-Polyglutamylatable Inhibitors of Dihydrofolate Reductase," *J. Med. Chem.*, 1991, vol. 34, pp. 222-227.

Abraham et al., "Aldehyde Oxidase Mediated 7-Hydroxylation of Antifolates and Its Therapeutic Relevance," *Cellular Pharmacology*, 1996, vol. 3, pp. 29-34.

(Continued)

*Primary Examiner* — Susanna Moore
(74) *Attorney, Agent, or Firm* — Womble Carlyle Sandridge & Rice, PLLC

(57) ABSTRACT

The present invention is directed to antifolate compounds having the structure

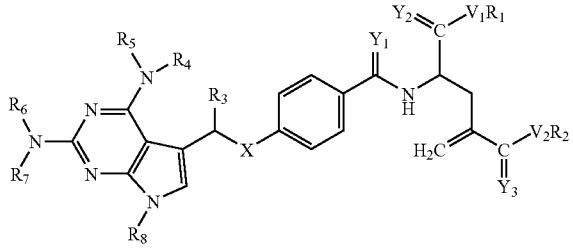

wherein:
X is $CHR_9$ or $NR_9$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;
$R_3$ is H, optionally substituted alkyl, optionally substituted alkenyl, optionally substituted alkynyl, optionally substituted alkoxy, hydroxyl, or halo; and
$R_4$, $R_5$, $R_6$, $R_7$, $R_8$, and $R_9$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, and prodrugs thereof. The compounds are useful in pharmaceutical compositions and in methods of treating multiple conditions, including abnormal cell proliferation, inflammatory diseases, asthma, and arthritis.

46 Claims, 1 Drawing Sheet

OTHER PUBLICATIONS

Alarcon et al., "Controlled Trial of Methotrexate Versus 10-Deazaaminopterin in the Treatment of Rheumatoid Arthristis," *Arthritis Rheumatism*, 1992, pp. 600-660, vol. 51, No. 5.

Amato et al., "Metabolism-Based Antifolate Drug Design: MDAM and MTREX," *Pharmacology and Therapeutics in the New Millennium*, 2001, pp. 204-212, Narosa Publishing House, New Delhi, India.

Baggott et al., "Folylpoly-γ-glutamates as Cosubstrates of 10-Formyltetrahdrofolate:5'- Phosphoribosy1-5amino-4-imidazole-Carboxamide Formyltransferase," *Biochemistry*, 1979, pp. 1036-1041, vol. 18, No. 1.

Baugh et al., "Polygammaglutamyl Metabolites of Methotrexate," *Biochemical and Biophysical Research Communications*, 1973, pp. 27-34, vol. 52, No. 1.

Blakley, *The Biochemistry of Folic Acid and Related Pteridines*. 1969, Amsterdam Elsevier.

Broxterman et al., "Cancer Research 2001: Drug Resistance, New Targets and Drug Combinations," *Drug Resistance Updates*, 2001, vol. 4, pp. 197-209.

Bryant et al., "Metabolism-Blocked Antifolate-2," *Proc. Am. Assoc. Cancer Res.*, 1999, vol. 40, p. 293 (Abstract No. 1944).

Caperelli et al., "The Human Glycinamide Ribonucleotide Transformylase Domain: Purification, Characterization and Kinetic Mechanism," *Archives of Biochemistry and Biophysics*, 1997, pp. 98-103, vol. 341, No. 1.

Castaneda et al., "Controlled Trial of Methotrexate Versus CH-1504 in the Treatment of Rheumatoid Arthritis," *Journal of Rheumatology*, 2006, pp. 862-864, vol. 33, No. 1.

Clowes et al., "Prevention of Stenosis After Vascular Reconstruction: Pharmacologic Control of Intimal Hyperplasia—A Review," *Journal of Vascular Surgery*, 1991, pp. 885-890, vol. 13.

Degraw et al., "Synthesis and Antifolate Activity of 8,10-Dideazaminopterin," *J. Het. Chem.*, 1982, vol. 19, pp. 1587-1588.

Dolnick et al., "Human Thymidylate Synthetase Derived From Blast Cells of Patients With Acute Myelocytic Leukemia," *The Journal of Biological Chemistry*, 1977, pp. 7697-7703, vol. 252, No. 1.

Gahtan et al., "Inflammatory Pathogenesis in Alzheimer's Disease: Biological Mechanisms and Cognitive Sequeli," *Neuroscience and Biobehavioral Reviews*, 1999, pp. 615-633, vol. 23, No. 5.

Gangjee et al., "Nonclassical 2,4-Diamino-8-Deazafolate Analogues as Inhibitors of Dihydrofolate Reductases from Rat Liver, *Pneumocystis carinii*, and *Toxoplasma gondii*," *J. Med. Chem.*, 1996, vol. 39(9), pp. 1836-1845.

Gangjee et al., "Design, Synthesis, and Biological Activities of Classical N- {4-[2-(2-Amino-4-ethylpyrrolo[2,3-*d*]pyrimidin-5-yl)ethyl]benzoyl}-L-glutamic Acid and Its 6-Methyl Derivative as Potential Dual Inhibitors of Thymidylate Synthase and Dihydrofolate Reductase and as Potential Antitumor Agents," *J. Med. Chem.*, 2003, pp. 591-600, vol. 46, No. 4.

Gupta et al., "Inflammation and Alzheimer's Disease," *The International Journal of Clinical Practice*, 2003, pp. 36-39, vol. 57, No. 1.

Jackman, "Antifolate Drugs in Cancer Therapy," Book Review: *Reprints from Current Trends, Drug Discover Today*, 1999.

Johns et al., "Enzymic Oxidation of Methotrexiate and Aminopterin," *Life Sciences*, 1964, pp. 1383-1388, vol. 3.

Johns et al.,"Metabolism of Folate Antagonists," *Annals New York Academy of Sciences*, 1971, pp. 378-386, vol. 186.

Kisliuk, "Deaza Analogs of Folic Acid as Antitumor Agents," *Current Pharmaceutical Design*, 2003, vol. 9(31), pp. 2615-2625.

Kormeili et al., Psoriasis: Immunopathogenesis and Evolving Immunomodulators and Systemic Therapies; U.S. Experiences, *British Journal of Dermatology*, 2004, pp. 3-15, vol. 151, No. 1.

Lemanke, "Inflammation in Childhood Asthma and Other Wheezing Disorders," *Pediatrics*, 2002, pp. 368-372, vol. 109, No. 2.

Lim, et al., "Gene-Nutrient Interactions Among Determinants of Folate and One-Carbon Metabolism on the Risk of Non-Hodgkin Lymphoma: NCI-SEER Case-Control Study," *Blood*, 2007, pp. 3050-3059, vol. 109, No. 7.

Lind, "Circulating Markers of Inflammation and Atherosclerosis," *Atherosclerosis*, 2003, pp. 203-214, vol. 169, No. 2.

Lloyd et al., "Crystallization and Preliminary Crystallographic Analysis of Carboxypeptidase $G_2$ From *Pseudomonas* sp. Strain RS-16," *J. Mol. Biol.*, 1991, pp. 17-18, vol. 220.

Matherly et al., "Membrane Transport of Folates," *Vitam Horm*, 2003, pp. 403-456, vol. 66.

McCullough et al., "Purification and Properties of Carboxypeptidase G" *The Journal of Biological Chemistry*, 1971, pp. 7201-7213, vol. 246, No. 23.

McGuire et al., "Enzymatic Synthesis of Polyglutamate Derivatives of 7-Hydroxymethotrexatel," *Biochemical Pharmacology*, 1984, pp. 1355-1361, vol. 33, No. 8.

McGuire et al., "Biochemical and Growth Inhibitory Effects of the *erythro* and *threo* Isomers of γ-Fluoromethotrexate, a Methotrexate Analogue Defective in Polyglutamylation," *Cancer Research*, 1989, pp. 4517-4525, vol. 49, No. 12.

McGuire et al., "Biochemical and Growth Inhibition Studies of Methotrexate and Aminopterin Analogues Containing a Tetrazole Ring in Place of the γCarboxyl Group," *Cancer Research*, 1990, pp. 1726-1731, vol. 50.

McGuire et al., "Biochemical and Biological Properties of Methotrexate Analogs Containing D-glutamic Acid or D-erythro,threo-4-fluoroglutamic Acid," *Biochemical Pharmacology*, 1991, pp. 2400-2403, vol. 42, No. 12.

McGuire et al., "Novel 6,5-fused Ring Heterocyclic Antifolates: Biochemical and Biological Characterization," *Cancer Research*, 1994, pp. 2673-2679, vol. 54.

McGuire et al., "5-Amino-4-Imidazolecarboxamide Riboside Potentiates Both Transport of Reduced Folates and Antifolates by the Human Reduced Folate Carrier and Their Subsequent Metabolism," *Cancer Research*, 2006, pp. 3836-3844, vol. 66, No. 7.

McGuire, "Anticancer Antifolates: Current Status and Future Directions," *Current Pharmaceutical Design*, 2003, vol. 9(31), pp. 2593-2613.

Mirza et al., "The Absence of Reactive Astrocytosis in Indicative of a Unique Inflammatory Process in Parkinson's Disease," *Neuroscience*, 2000, pp. 425-432, vol. 95, No. 2.

Montgomery et al., "Design and Synthesis of Folate Analogs as Antimetabolites in Folate Antagonists as Therapeutic Agents," *Biochemistry, Molecular Actions and Synthetic Designs*, 1984, pp. 219-261, vol. 1.

Moran et al. "Relative Substrate Activities of Structurally Related Pteridine, Quinazoline, and Pyrimidine Analogs for Mouse Liver Folylpolyglutamate Synthetase," *Molecular Pharmacology*, 1989, pp. 736-743, vol. 36, No. 5.

Nagayama et al., "Eosinophils and Basophilic Cells in Sputum and Nasal Smears Taken from Infants and Young Children during Acute Asthma," *Pediatr. Allergy Immunol.*, 1995, vol. 6, pp. 204-208.

Nair et al., "Folate Analogues. 34. Synthesis and Antitumor Activity of Non-Polyglutamylatable Inhibitors of Dihydrofolate Reductase," *J. Med. Chem*, 1991, pp. 222-227, vol. 34.

Nair et al., "Polyglutamylation as a Determinant of Cytotoxicity of Classical Folate Analogue Inhibitors of Thymidylate Synthase and Glycinamide Ribonucleotide Formyltransferase," *Cellular Pharmacology*, 1994, vol. 1, pp. 245-249.

Nair et al., "Aldehyde Oxidase Mediated 7-Hydroxylation of Antifolates and its Therapeutic Relevance," *Cellular Pharmacology*, 1996, pp. 29-34, vol. 3.

Nair et al., "Metabolism-Blocked Antifolates-1," *Proc. Am. Assoc. Cancer Res.*, 1998, vol. 39, p. 431 (Abstract No. 2938).

Nair et al., "Metabolism Blocked Classical Folate Analog Inhibitors of Dihydrofolate Reductase-1: Synthesis and Biological Evaluation of Mobiletrex," *Medicinal Chemistry Research*, 1999, pp. 176-185, vol. 9, No. 3.

Nair et al., "Metabolism-Blocked Antifolates, 3: Enantiomers of 4'methylene-5,8,10-Trideazaaminopterin (M-Trex)," *Proceedings of the American Association for Cancer Research Annual Meeting*, 2001, pp. 294, vol. 42 (Abstract No. 1583).

Renouard et al., "Functionalized Tetradentate Ligands for Ru-Sensitized Solar Cells," *Tetrahedron*, 2001, vol. 57, pp. 8145-8150.

Rosowsky et al., "Analogues of Methotrexate and Aminopterin with γ-Methylene and γ-Cyano Substitution of the Glutamate Side Chain: Synthesis and in Vitro Biological Activity," *J. Med. Chem.*, 1991, vol. 34, pp. 203-208.

Ross, "Atherosclerosis—An Inflammatory Disease," *New England Journal of Medicine*, 1999, pp. 115-126, vol. 340.

Sherwood et al., "Purification and Properties of Carboxypeptidase G2 From *Pseudomonas* sp. Strain RS-16," *Eur. J Biochem.*, 1985, pp. 447-453, vol. 148.

Shilai et al., "Selective Metallation of Thiophene and Thiazole Rings with Magnesium Amide Base," *J. Chem. Soc., Perkin Trans. I*, 2001, pp. 442-444.

Takimoto, "New Antifolates: Pharmacology and Clinical Applications," *The Oncologist*, 1996, pp. 68-81, vol. 1.

Van Triest et al., "Downstream Molecular Determinants of Response to 5-Fluorouracil and Antifolate Thymidylate Synthase Inhibitors," *Annals of Oncology*, 2000, pp. 385-391, vol. 11.

Yan et al., "Folic Acid Analogs . III. N-(2-[2-(4-diamino-6-quinazolinyl)ethyl] benzoyl)-L-glutamic acid," *J. Heterocyclic Chem.*, 1979, 541-544, vol. 16.

SUBSTITUTED PYRROLO[2,3-D]PYRIMIDINES AS ANTIFOLATES

CROSS-REFERENCE TO RELATED APPLICATIONS

The present patent application claims priority to U.S. Provisional Patent Application No. 60/885,719, filed Jan. 19, 2007, which is incorporated herein by reference in its entirety.

FIELD OF THE INVENTION

The present application is directed to pharmaceutically active compounds and specifically to new classical antifolate compounds.

BACKGROUND

Folic acid is a water-soluble B vitamin known by the systematic name N-[4(2-amino-4-hydroxy-pteridin-6-ylmethylamino)-benzoyl]-L(+)-glutamic acid and having the structure provided below in Formula (1).

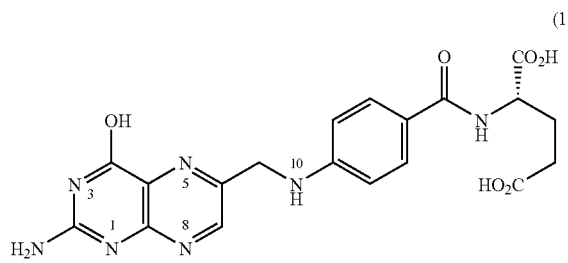

(1)

As seen in Formula (1), the folic acid structure can generally be described as being formed of pteridine ring, a para-aminobenzoic acid moiety, and a glutamate moiety. Folic acid and its derivatives are necessary for metabolism and growth, particularly participating in the body's synthesis of thymidylate, amino acids, and purines. Derivatives of folic acid, such as naturally occurring folates, are known to have biochemical effects comparable to folic acid. Folic acid is known to be derivatized via hydrogenation, such as at the 1,4-diazine ring, or being methylated, formaldehydylated, or bridged, wherein substitution is generally at the $N^5$ or $N^{10}$ positions. Folates have been studied for efficacy in various uses including reduction in severity or incidence of birth defects, heart disease, stroke, memory loss, and age-related dementia.

Antifolate compounds, like folates, are structurally similar to folic acid; however, antifolate compounds function to disrupt folic acid metabolism. A review of antifolates is provided by Takamoto (1996) *The Oncologist*, 1:68-81, which is incorporated herein by reference. One specific group of antifolates, the so-called "classical antifolates," is characterized by the presence of a folic acid p-aminobenzoylglutamic acid side chain, or a derivative of that side chain. Another group of antifolates, the so-called "nonclassical antifolates," are characterized by the specific absence of the p-aminobenzoylglutamic group. Because antifolates have a physiological effect that is opposite the effect of folic acid, antifolates have been shown to exhibit useful physiological functions, such as the ability to destroy cancer cells by causing apoptosis.

Folate monoglutamylates and antifolate monoglutamylates are transported through cell membranes either in reduced form or unreduced form by carriers specific to those respective forms. Expression of these transport systems varies with cell type and cell growth conditions. After entering cells most folates, and many antifolates, are modified by polyglutamylation, wherein one glutamate residue is linked to a second glutamate residue at the α carboxy group via a peptide bond. This leads to formation of poly-L-γ-glutamylates, usually by addition of three to six glutamate residues. Enzymes that act on folates have a higher affinity for the polyglutamylated forms. Therefore, polyglutamylated folates generally exhibit a longer retention time within the cell.

An intact folate enzyme pathway is important to maintain de novo synthesis of the building blocks of DNA, as well as many important amino acids. Antifolate targets include the various enzymes involved in folate metabolism, including (i) dihydrofolate reductase (DHFR); (ii) thymidylate synthase (TS); (iii) folylpolyglutamyl synthase; and (iv) glycinamide ribonucleotide transformylase (GARFT) and aminoimidazole carboxamide ribonucleotide transformylase (AICART).

The reduced folate carrier (RFC), which is a transmembrane glycoprotein, plays an active role in the folate pathway transporting reduced folate into mammalian cells via the carrier mediated mechanism (as opposed to the receptor mediated mechanism). The RFC also transports antifolates, such as methotrexate. Thus, mediating the ability of RFC to function can affect the ability of cells to uptake reduced folates.

Polyglutamylated folates can function as enzyme cofactors, whereas polyglutamylated antifolates generally function as enzyme inhibitors. Moreover, interference with folate metabolism prevents de novo synthesis of DNA and some amino acids, thereby enabling antifolate selective cytotoxicity. Methotrexate, the structure of which is provided in Formula (2), is one antifolate that has shown use in cancer treatment, particularly treatment of acute leukemia, non-Hodgkin's lymphoma, breast cancer, head and neck cancer, choriocarcinoma, osteogenic sarcoma, and bladder cancer.

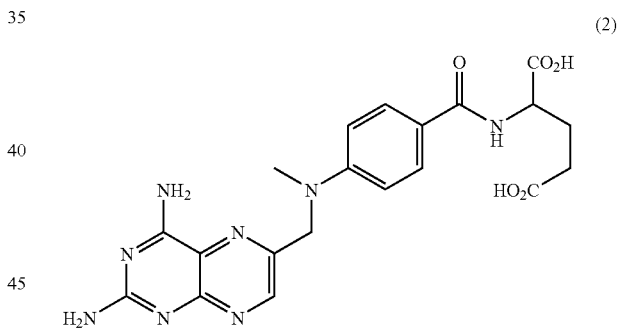

(2)

Nair et al. (*J. Med. Chem.* (1991) 34:222-227), incorporated herein by reference, demonstrated that polyglutamylation of classical antifolates was not essential for anti-tumor activity and may even be undesirable in that polyglutamylation can lead to a loss of drug pharmacological activity and target specificity. This was followed by the discovery of numerous nonpolyglutamylatable classical antifolates. See Nair et al. (1998) *Proc. Amer. Assoc. Cancer Research* 39:431, which is incorporated herein by reference. One particular group of nonpolyglutamylatable antifolates are characterized by a methylidene group (i.e., a =$CH_2$ substituent) at the 4-position of the glutamate moiety. The presence of this chemical group has been shown to affect biological activity of the antifolate compound. See Nair et al. (1996) *Cellular Pharmacology* 3:29, which is incorporated herein by reference.

Further folic acid derivatives have also been studied in the search for antifolates with increased metabolic stability allowing for smaller doses and less frequent patient administration. For example, a dideaza (i.e., quinazoline-based) analog has been shown to avoid physiological hydroxylation on the pteridine ring system. Furthermore, replacement of the secondary amine nitrogen atom with an optionally substituted carbon atom has been shown to protect neighboring bonds from physiological cleavage.

One example of an antifolate having carbon replacement of the secondary amine nitrogen is 4-amino-4-deoxy-10-deazapteroyl-γ-methyleneglutamic acid—more commonly referred to as MDAM—the structure of which is provided in Formula (3).

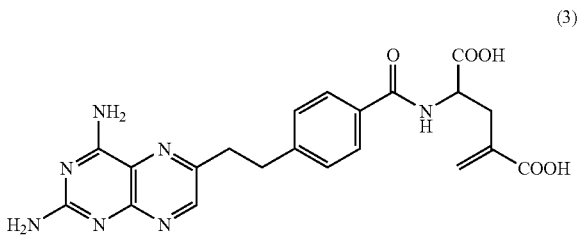

(3)

The L-enantiomer of MDAM has been shown to exhibit increased physiological activity. See U.S. Pat. No. 5,550,128, which is incorporated herein by reference. Another example of a classical antifolate designed for metabolic stability is ZD1694, which is shown in Formula (4).

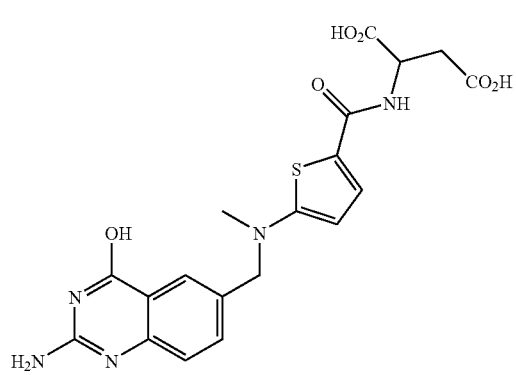

(4)

A group of antifolate compounds according to the structure shown in Formula (5) combines several of the molecular features described above, and this group of compounds is known by the names MobileTrexate, Mobile Trex, Mobiltrex, or M-Trex.

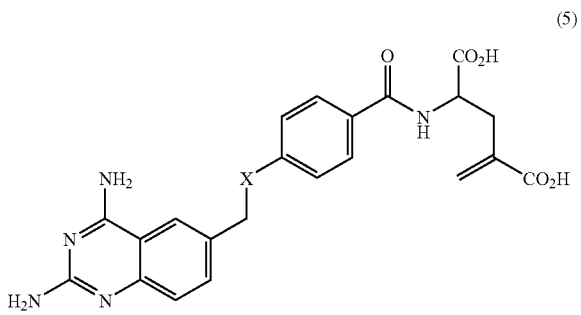

(5)

As shown in Formula (5), M-Trex encompasses a group of compounds wherein X can be $CH_2$, $CHCH_3$, $CH(CH_2CH_3)$, NH, or $NCH_3$. As disclosed in U.S. Pat. No. 5,912,251, which is incorporated herein by reference, the M-TREX species wherein $X=CH_2$ has shown activity for the treatment of abnormal cellular proliferation, inflammation disorders and autoimmune diseases. This compound, which is shown in Formula (6), is known by various names, including the following: 2-{4-[2-(2,4-diamino-quinazolin-6-yl)-ethyl]-benzoylamino}-4-methylidene-pentanedioic acid; gamma methylene glutamate 5,8,10-trideaza aminopterin; and 5,8-dideaza MDAM. The compound of Formula (6) is non-polyglutamylatable, non-hydroxylatable, and capable of disrupting folate metabolism. The compound has also shown effectiveness in killing large numbers of human leukemia cells and human solid tumor cells in culture at therapeutically relevant concentrations, and has further shown activity as an anti-inflammatory agent in an animal model of asthma.

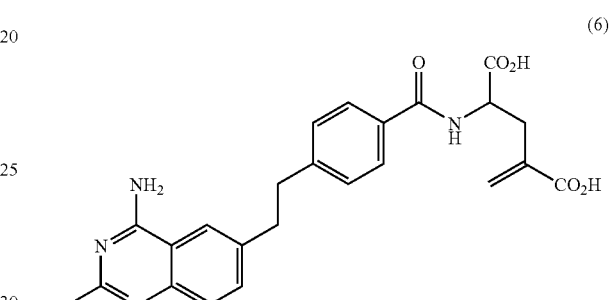

(6)

The effectiveness of antifolates as pharmaceutical compounds arises from other factors in addition to metabolic inertness, as described above. The multiple enzymes involved in folic acid metabolism within the body present a choice of inhibition targets for antifolates. In other words, it is possible for antifolates to vary as to which enzyme(s) they inhibit. For example, some antifolates inhibit primarily dihydrofolate reductase (DHFR), while other antifolates inhibit primarily thymidylate synthase (TS), glycinamide ribonucleotide formyltransferase (GARFT), or aminoimidazole carboxamide ribonucleotide transformylase, while still other antifolates inhibit combinations of these enzymes. This "choice" of enzyme inhibition is illustrated in FIG. 1.

Antifolates can vary substantially in their efficacy and specificity. Moreover, there is a continuing need for antifolate improvements, such as reduced toxicity levels, increased shelf life, and ease of delivery to target sites in the body. As it is difficult to predict reliably the full scope of physiological properties in advance of testing each actual compound, there also remains a need for improvements in antifolate design.

SUMMARY OF THE INVENTION

The present invention provides novel classical antifolate compounds with improved properties. The invention also provides pharmaceutical compositions comprising such compounds and methods for synthesizing such compounds. The invention further provides methods of treatment for various conditions and diseases including, but not limited to, abnormal cellular proliferation, asthma and other inflammatory diseases, and rheumatoid arthritis and other autoimmune diseases.

In one embodiment, the present invention is directed to novel classical antifolate compounds having the structure provided in Formula (7)

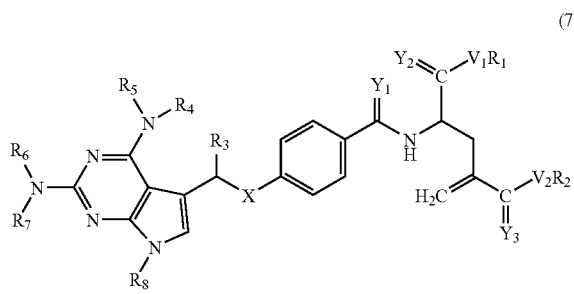

(7)

wherein:

X is CHR$_9$ or NR$_9$;

Y$_1$, Y$_2$, and Y$_3$ independently are O or S;

V$_1$ and V$_2$ independently are O, S, or NZ;

Z is H, optionally substituted alkyl, optionally substituted alkenyl, optionally substituted alkynyl, or alkaryl;

R$_1$ and R$_2$ independently are H, optionally substituted alkyl, optionally substituted alkenyl, optionally substituted alkynyl, or alkaryl;

R$_3$ is H, optionally substituted alkyl, optionally substituted alkenyl, optionally substituted alkynyl, optionally substituted alkoxy, hydroxyl, or halo; and R$_4$, R$_5$, R$_6$, R$_7$, R$_8$, and R$_9$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, enantiomers, and prodrugs thereof.

In certain embodiments, the compounds provided according to the invention have a terminus that is substantially a glutamate moiety. For example, the compounds can be according to Formula (8)

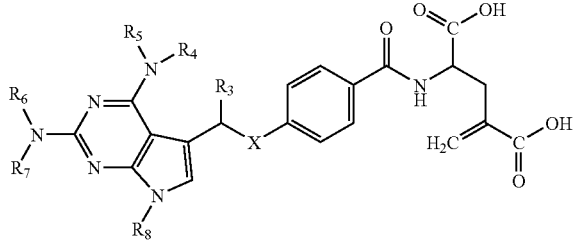

(8)

wherein:

X is CHR$_9$ or NR$_9$;

R$_3$ is H, optionally substituted alkyl, optionally substituted alkenyl, optionally substituted alkynyl, optionally substituted alkoxy, hydroxyl, or halo; and R$_4$, R$_5$, R$_6$, R$_7$, R$_8$, and R$_9$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, enantiomers, or prodrugs thereof.

In further embodiments, the compounds provided according to the invention have a terminus that is substantially a diamino-pyrrolopyrimidine moiety. For example, the compounds can be according to Formula (10)

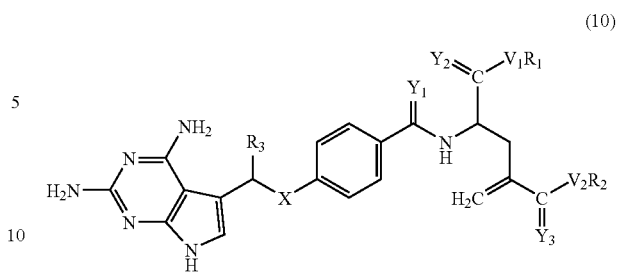

(10)

wherein:

X is CHR$_9$ or NR$_9$;

Y$_1$, Y$_2$, and Y$_3$ independently are O or S;

V$_1$ and V$_2$ independently are O, S, or NZ;

Z is H, optionally substituted alkyl, optionally substituted alkenyl, optionally substituted alkynyl, or alkaryl;

R$_1$ and R$_2$ independently are H, optionally substituted alkyl, optionally substituted alkenyl, optionally substituted alkynyl, or alkaryl;

R$_3$ is H, optionally substituted alkyl, optionally substituted alkenyl, optionally substituted alkynyl, optionally substituted alkoxy, hydroxyl, or halo; and R$_9$ is H, optionally substituted alkyl, optionally substituted alkenyl, optionally substituted alkynyl, acyl, —C(O)-alkyl, —C(O)-alkenyl, or —C(O)-alkynyl; as well as pharmaceutically acceptable esters, amides, salts, solvates, enantiomers, or prodrugs thereof.

In one embodiment, the invention provides compounds according to Formula (11)

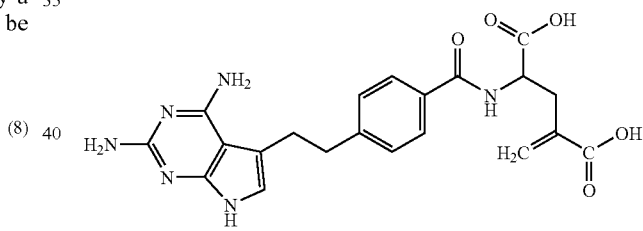

(11)

or pharmaceutically acceptable esters, amides, salts, solvates, enantiomers, or prodrugs thereof.

In specific embodiments, the novel antifolate compounds are in the form of pharmaceutically acceptable salts. In particular, the compounds may be in the form of an alkali-metal salt. In one specific embodiment, the present invention is directed to an antifolate compound according to Formula (12), which is in the form of a disodium salt, or an enantiomer thereof.

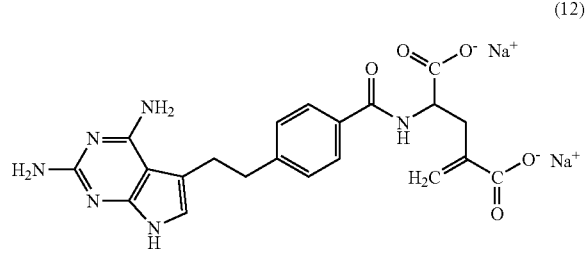

(12)

According to other embodiments, the present invention is directed to pharmaceutical compositions comprising one or more compounds disclosed herein. For example, the invention provides a pharmaceutical composition comprising a compound according to Formula (7). In a particular embodiment, the invention provides pharmaceutical compositions comprising the compound according to Formula (7) wherein X is $CH_2$, $Y_1$, $Y_2$, and $Y_3$ are O, $V_1$ and $V_2$ are O, $R_1$ and $R_2$ are H, $R_3$ is H, $R_4$ is H, $R_5$ is H, $R_6$ is H, $R_7$ is H, and $R_8$ is H. In still other embodiments, the pharmaceutical compositions of the invention comprise compounds as described herein that are in the form of a pharmaceutically acceptable salt, such as an alkali metal salt, particularly a disodium salt. In further embodiments, the invention provides pharmaceutical compositions comprising one or more compounds as described herein in combination with one or more further active ingredients.

The present invention further provides various methods of treatment comprising administering one or more compounds according to the invention, alone or in combination with one or more further active ingredients. In certain embodiments, the invention provides methods for treating conditions such as abnormal cell proliferation, inflammation, arthritis, and asthma. Accordingly, the invention provides a method for treating a condition selected from the group consisting of abnormal cell proliferation, inflammation, asthma, and arthritis, wherein the method comprises administering to a subject in need of treatment an amount of a compound according to the invention therapeutically effective for treating abnormal cell proliferation, inflammation, asthma, or arthritis.

BRIEF DESCRIPTION OF THE DRAWINGS

Figure 1:
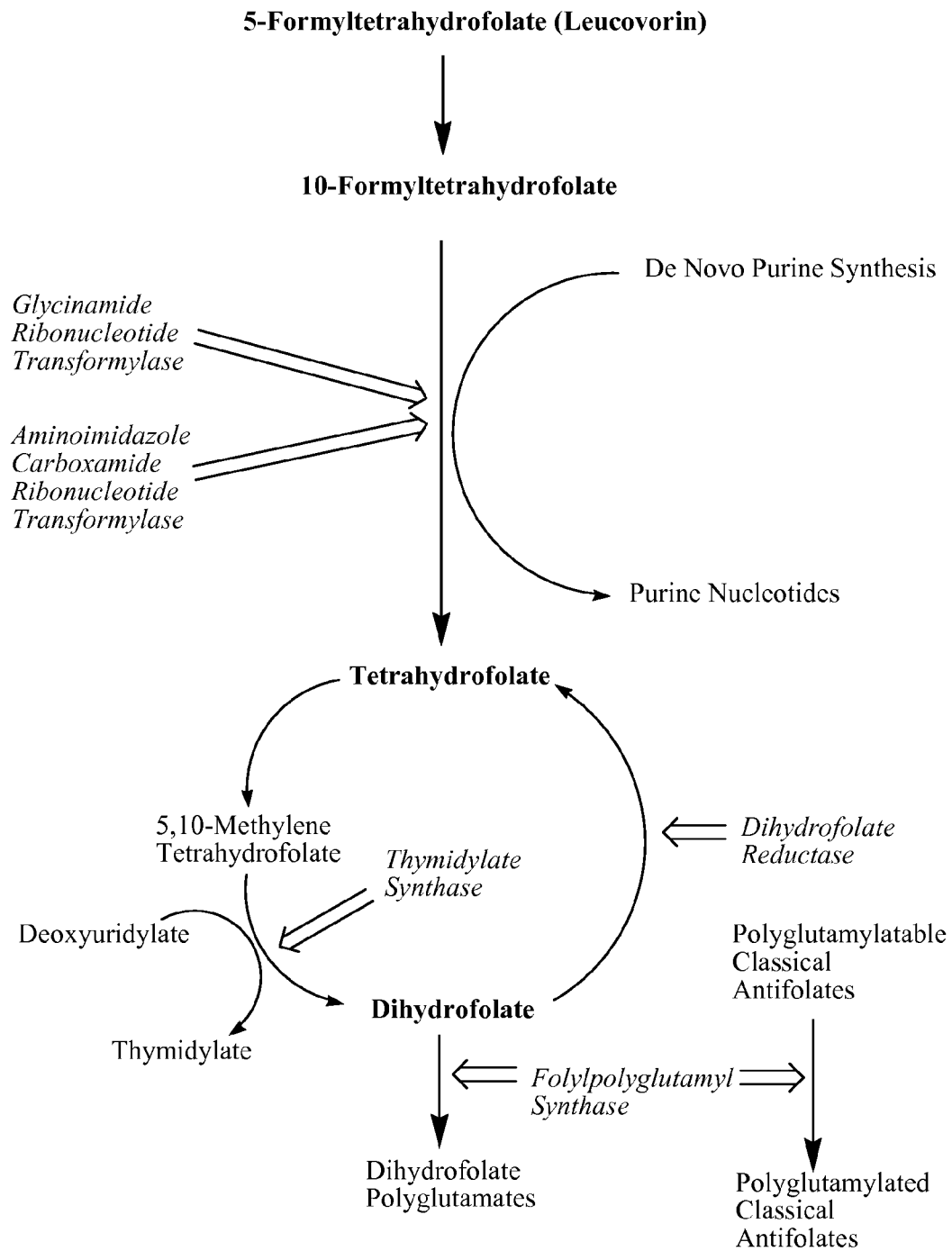

Having thus described the invention in general terms, reference will now be made to the accompanying drawing, which is not necessarily drawn to scale, and wherein:

FIG. 1 is a schematic representation of the metabolic pathway of folate compounds and the interaction with polyglutamylatable classical antifolates.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides new classical antifolates and methods of preparation thereof. These new compounds can be used in pharmaceutical compositions, either directly or in the form of their pharmaceutically active esters, amides, salts, solvates, or prodrugs. The novel compounds are useful in the treatment of a number of conditions and diseases, particularly for the treatment of abnormal cell proliferation, inflammation, arthritis, or asthma.

I. Definitions

The term "metabolically inert antifolate" as used herein means compounds that are (i) folic acid analogs capable of disrupting folate metabolism and (ii) non-polyglutamylatable. In certain embodiments, the term can mean compounds that are also (iii) non-hydroxylatable.

The term "alkali metal" as used herein means Group IA elements and particularly includes sodium, lithium, and potassium; the term "alkali metal salt" as used herein means an ionic compound wherein the cation moiety of the compound comprises an alkali metal, particularly sodium, lithium, or potassium.

The term "alkyl" as used herein means saturated straight, branched, or cyclic hydrocarbon groups. In particular embodiments, alkyl refers to groups comprising 1 to 10 carbon atoms ("$C_{1-10}$ alkyl"). In further embodiments, alkyl refers to groups comprising 1 to 8 carbon atoms ("$C_{1-8}$ alkyl"), 1 to 6 carbon atoms ("$C_{1-6}$ alkyl"), or 1 to 4 carbon atoms ("$C_{1-4}$ alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethybutyl, and 2,3-dimethylbutyl. Substituted alkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 1 to 10 carbon atoms ("$C_{1-10}$ alkenyl"). In further embodiments, alkyl refers to groups comprising 1 to 8 carbon atoms ("$C_{1-8}$ alkenyl"), 1 to 6 carbon atoms ("$C_{1-6}$ alkenyl"), or 1 to 4 carbon atoms ("$C_{1-4}$ alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 1 to 10 carbon atoms ("$C_{1-10}$ alkynyl"). In further embodiments, alkyl refers to groups comprising 1 to 8 carbon atoms ("$C_{1-8}$ alkynyl"), 1 to 6 carbon atoms ("$C_{1-6}$ alkynyl"), or 1 to 4 carbon atoms ("$C_{1-4}$ alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("$C_{1-10}$ alkoxy"). In further embodiments, alkoxy refers to oxygen-linked groups comprising 1 to 8 carbon atoms ("$C_{1-8}$ alkoxy"), 1 to 6 carbon atoms ("$C_{1-6}$ alkoxy"), or 1 to 4 carbon atoms ("$C_{1-4}$ alkoxy").

The term "halo" or "halogen" as used herein means fluorine, chlorine, bromine, or iodine.

The term "aryl" as used herein means a stable monocyclic, bicyclic, or tricyclic carbon ring of up to 8 members in each ring, wherein at least one ring is aromatic as defined by the Huickel 4n+2 rule. Exemplary aryl groups according to the invention include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, $C_1$-$C_6$ alkyl or $C_1$-$C_6$ alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl. Aryl groups in the esters optimally comprise a phenyl group.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal.

The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "antiproliferative agent" as used herein means a compound that decreases the hyperproliferation of cells.

The term "abnormal cell proliferation" as used herein means a disease or condition characterized by the inappropriate growth or multiplication of one or more cell types relative to the growth of that cell type or types in an individual not suffering from that disease or condition.

The term "cancer" as used herein means a disease or condition characterized by uncontrolled, abnormal growth of cells, which can spread locally or through the bloodstream and lymphatic system to other parts of the body. The term includes both tumor-forming or non-tumor forming cancers, and includes various types of cancers, such as primary tumors and tumor metastasis.

The term "tumor" as used herein means an abnormal mass of cells within a multicellular organism that results from excessive cell division that is uncontrolled and progressive, also called a neoplasm. A tumor may either be benign or malignant.

The term "fibrotic disorders" as used herein means fibrosis and other medical complications of fibrosis which result in whole or in part from the proliferation of fibroblasts.

The term "arthritis" as used herein means an inflammatory disorder affecting joints that can be infective, autoimmune, or traumatic in origin.

II. Compounds

The compounds of the present invention comprise metabolically inert antifolates. As recognized in the art, antifolates are compounds that interfere with various stages of folate metabolism. Thus, the compounds of the invention can particularly be used in pharmaceutical preparations useful for the treatment of diseases and conditions related to or capable of being treated by disruption of folate metabolism, or other biological mechanisms related to folate metabolism.

In one embodiment, the novel compounds of the present invention comprise compounds having the structure provided in Formula (7),

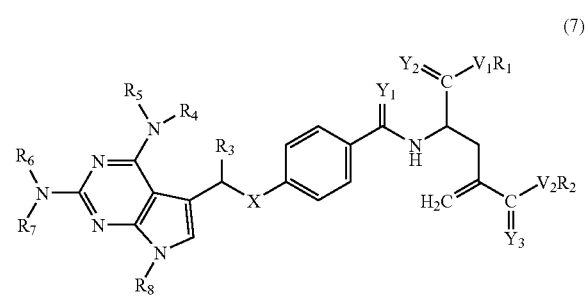

(7)

wherein:

X is $CHR_9$ or $NR_9$;

$Y_1$, $Y_2$, and $Y_3$ independently are O or S;

$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, $R_8$, and $R_9$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, and prodrugs thereof.

In another embodiment, the novel compounds of the present invention comprise compounds having the structure provided in Formula (8)

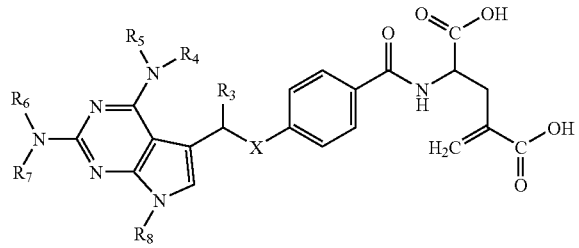

(8)

wherein:

X is $CHR_9$ or $NR_9$;

$R_3$ is H, optionally substituted alkyl, optionally substituted alkenyl, optionally substituted alkynyl, optionally substituted alkoxy, hydroxyl, or halo; and $R_4$, $R_5$, $R_6$, $R_7$, $R_8$, and $R_9$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, and prodrugs thereof.

In still another embodiment, the novel compounds of the present invention comprise compounds having the structure provided in Formula (9)

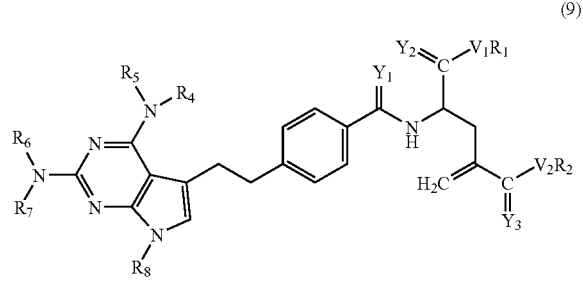

(9)

wherein:

$Y_1$, $Y_2$, and $Y_3$ independently are O or S;

$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl; and $R_4$, $R_5$, $R_6$, $R_7$ and $R_8$ independently are H, optionally substituted alkyl, optionally substituted alkenyl, optionally substituted alkynyl, acyl, —C(O)-alkyl, —C(O)-alkenyl, or —C(O)—alkynyl; as well as pharmaceutically acceptable esters, amides, salts, solvates, and prodrugs thereof.

In yet another embodiment, the novel compounds of the present invention comprise compounds having the structure provided in Formula (10)

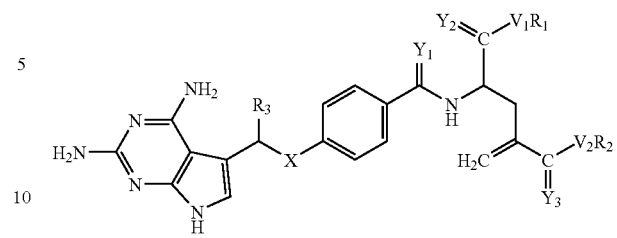

(10)

wherein:

X is $CHR_9$ or $NR_9$;

$Y_1$, $Y_2$, and $Y_3$ independently are O or S;

$V_1$ and $V_2$ independently are O, S, or NZ;

Z is H, optionally substituted alkyl, optionally substituted alkenyl, optionally substituted alkynyl, or alkaryl;

$R_1$ and $R_2$ independently are H, optionally substituted alkyl, optionally substituted alkenyl, optionally substituted alkynyl, or alkaryl;

$R_3$ is H, optionally substituted alkyl, optionally substituted alkenyl, optionally substituted alkynyl, optionally substituted alkoxy, hydroxyl, or halo; and $R_9$ is H, optionally substituted alkyl, optionally substituted alkenyl, optionally substituted alkynyl, acyl, —C(O)-alkyl, —C(O)-alkenyl, or —C(O)-alkynyl as well as pharmaceutically acceptable esters, amides, salts, solvates, and prodrugs thereof.

With respect to Formulas (7)-(10), preferred examples of X include —$CH_2$—, —NH—, —CH($C_{1-6}$ alkyl)—, —N($C_{1-6}$ alkyl)—, —CH(C(O)—$C_{1-6}$ alkyl)—, and —N(C(O)—$C_{1-6}$ alkyl)—; preferred examples of Z include H and $C_{1-6}$ alkyl; preferred examples of $R_1$ and $R_2$ independently include H and $C_{1-6}$ alkyl; preferred examples of $R_3$ include H, $C_{1-6}$ alkyl, hydroxyl, and halo; and preferred examples of $R_4$, $R_5$, $R_6$, $R_7$, $R_8$, and $R_9$ independently include H, $C_{1-6}$ alkyl, and —C(O)—$C_{1-6}$ alkyl, wherein each $C_{1-6}$ alkyl can be optionally substituted with one or more halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

In one particular embodiment, the present invention provides a novel classical antifolate compound having the structure provided in Formula (11), may be referred to herein as CHL-003. The asterisk in Formula (11) indicates a chiral atom. As more fully described below, this point of chirality can be the focus for the preparation of enantiomerically purified forms of the compound. In the absence of specific identification of an enantiomerically purified form, the compound would be expected to be in the racemic form.

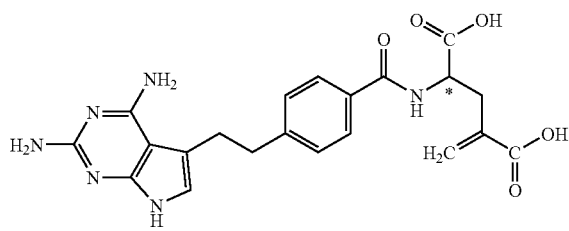

(11)

Various processes for synthesizing antifolate compounds are disclosed in U.S. Pat. Nos. 4,996,207, 5,550,128, 5,593,999, Abraham et al. (1991) *J. Med. Chem.* 34:222-227, and Rosowsky et al. (1991) *J. Med. Chem.* 34:203-208, all of which are incorporated herein by reference. As one example of a method of synthesis, the compound according to Formula (11) can be prepared according to Reaction Scheme I, shown below, wherein X is a halogen.

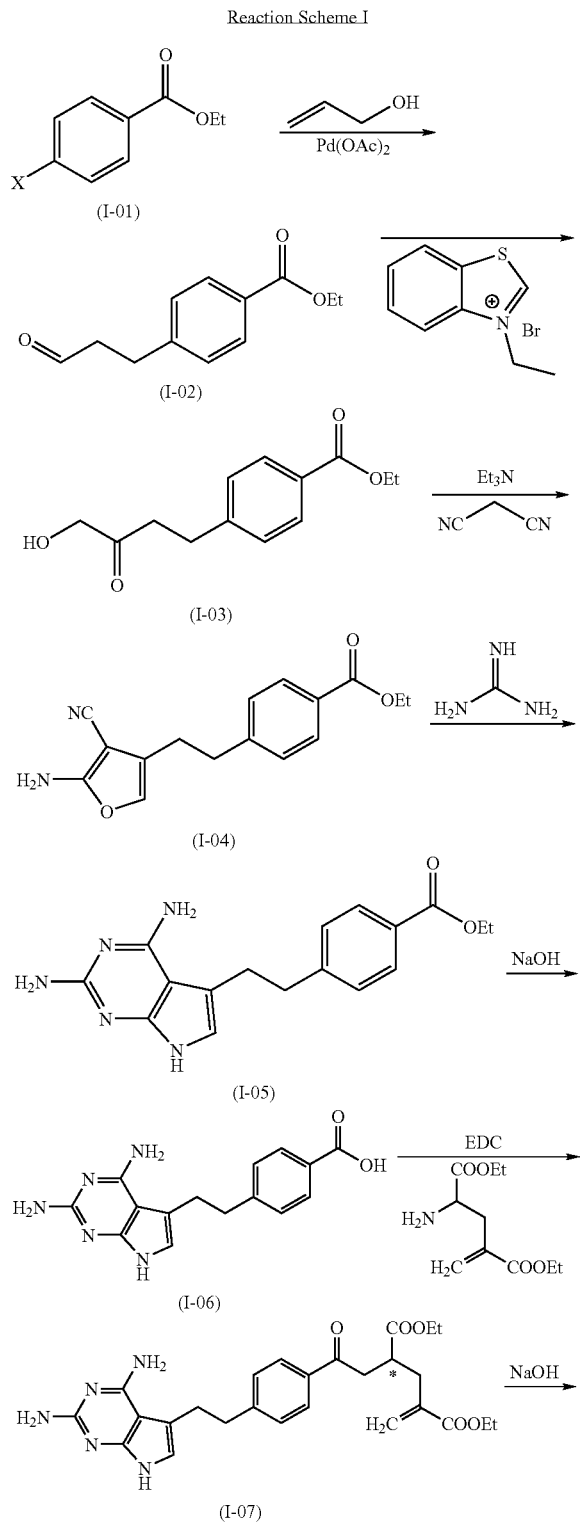

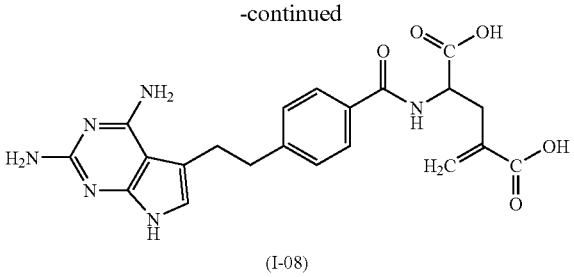

III. Biologically Active Variants

Biologically active variants of the compounds set forth above are particularly also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to one embodiment of the invention, suitable biologically active variants comprise one or more analogues or derivatives of the compounds described above. Indeed, a single compound, such as those described above, may give rise to an entire family of analogues or derivatives having similar activity and, therefore, usefulness according to the present invention. Likewise, a single compound, such as those described above, may represent a single family member of a greater class of compounds useful according to the present invention. Accordingly, the present invention fully encompasses not only the compounds described above, but analogues and derivatives of such compounds, particularly those identifiable by methods commonly known in the art and recognizable to the skilled artisan.

The compounds disclosed herein may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i. e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The antifolate compounds of the invention may be provided in an enantiomerically enriched form, such as a mixture of enantiomers in which one enantiomer is present in excess (given as a mole fraction or a weight fraction). Enantiomeric excess is understood to exist where a chemical substance comprises two enantiomers of the same compound and one enantiomer is present in a greater amount than the other enantiomer. Unlike racemic mixtures, these mixtures will show a net optical rotation. With knowledge of the specific rotation of the mixture and the specific rotation of the pure enantiomer, the enantiomeric excess (abbreviated "ee") can be determined by known methods. Direct determination of the quantities of each enantiomer present in the mixture is possible with NMR spectroscopy and chiral column chromatography.

Referring to Formula (11), the compounds of the invention can be provided in the racemic form or enantiomerically purified for the (R) or (S) isomer. Example 2 below describes the synthesis of the enantiomerically purified (S) isomer of the compound of Formula (12). Example 3 describes the synthesis of the racemic form of the compound of Formula (11).

In specific embodiments, the compounds of the invention can comprise an antifolate compound having an enantiomeric purity for a single enantiomer of at least about 75%. In further embodiments, the antifolate compound of the invention has an enantiomeric purity of at least about 80%, at least about 85%, at least about 90%, at least about 95%, at least about 96%, at least about 97%, at least about 98%, at least about 99%, or at least about 99.5%. In one embodiment, the compounds of the invention comprise an antifolate compound having such enantiomeric purity for the (S) isomer. In another embodiment, the compounds of the invention comprise an antifolate compound having such enantiomeric purity for the (R) isomer. In a specific embodiment, the invention encompasses the compound (S)-N-{4-[2-(2,4-diamino-7H-pyrrolo[2,3-d]pyrimidin-5-yl)ethyl]benzoyl}-4-methylene-L-glutamic acid disodium salt.

The compounds described herein can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, 4$^{th}$ Ed. (New York: Wiley-Interscience, 1992), which is incorporated herein by reference.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like.

Esters of the compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0 ° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the compositions of the invention may exist in different forms. For example, the compounds may exist in stable and metastable crystalline forms and isotropic and amorphous forms, all of which are intended to be within the scope of the present invention.

If a compound useful according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound of the invention is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

In one particular embodiment, an antifolate compound according to the invention is in the form of a salt. For example, the compound can be a compound according to Formula (7), Formula (9), or Formula (10), wherein one or all of $R_1$, $R_2$, and Z are replaced by a suitable salt-forming cation. Preferentially, the salt is an alkali metal salt, particularly sodium or potassium. In specific embodiments, the salt is a disodium salt. A particularly preferred disodium salt useful in the pharmaceutical compositions of the invention is provided below in Formula (12). Of course, it is understood that other cationic moieties, particularly other alkali metals, could be used in the salt compound. For example, in one particular embodiment, the invention encompasses a potassium salt of the compound according to Formula (11). One method for the synthesis of the compound of Formula (12) is described below in Example 2.

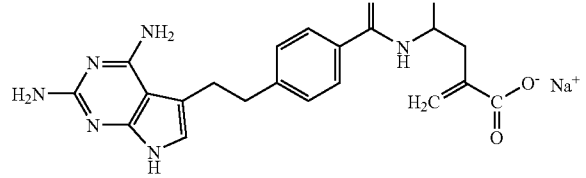

(12)

In one specific embodiment, the compound of Formula (12) is provided in the enantiomerically purified (S) form. In particular, the invention encompasses (S)-N-{4-[2-(2,4-diamino-7H-pyrrolo[2,3-d]pyrimidin-5-yl)ethyl]benzoyl}-4-methylene-L-glutamic acid disodium salt (which may be referred to herein as CHL1007).

The present invention further includes prodrugs and active metabolites of the compounds of the invention. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. In preferred embodiments, the compounds of this invention possess anti-proliferative activity against abnormally proliferating cells, or are metabolized to a compound that exhibits such activity.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed compounds to achieve a desired effect.

IV. Pharmaceutical Compositions

While it is possible for the individual compound used in the composition of the present invention to be administered in the raw chemical form, it is preferred for the compounds to be delivered as a pharmaceutical composition. Accordingly, there are provided by the present invention pharmaceutical compositions comprising one or more compounds as described herein. As such, the compositions of the present invention comprise the pharmaceutically active compounds, as described above, or pharmaceutically acceptable esters, amides, salts, solvates, analogs, derivatives, or prodrugs thereof. Further, the inventive compositions can be prepared and delivered in a variety of combinations. For example, the composition can comprise a single composition containing all of the active ingredients. Alternately, the composition can comprise multiple compositions comprising separate active ingredients but intended to be administered simultaneously, in succession, or in otherwise close proximity of time.

The compounds of the invention can be prepared and delivered together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Compositions of the present invention may include short-term, rapid-onset, rapid-offset, controlled release, sustained release, delayed release, and pulsatile release compositions, providing the compositions achieve administration of a compound as described herein. See *Remington's Pharmaceutical Sciences* (18$^{th}$ ed.; Mack Publishing Company, Eaton, Penn., 1990), herein incorporated by reference in its entirety. Pharmaceutical compositions according to the present invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrastemal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts. Generally speaking, such methods of preparation comprise combining (by various methods) the active compounds of the invention with a suitable carrier or other adjuvant, which may consist of one or more ingredients. The combination of the active ingredients with the one or more adjuvants is then physically treated to present the composition in a suitable form for delivery (e.g., shaping into a tablet or forming an aqueous suspension).

Pharmaceutical compositions according to the present invention suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention.

In one embodiment, compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the compound may be made using a physiologically degradable composition, such as gelatin. Such hard capsules comprise the compound, and may further comprise additional ingredients including, for example, an inert solid diluent such as calcium carbonate, calcium phosphate, or kaolin. Soft gelatin capsules containing the compound may be made using a physiologically degradable composition, such as gelatin. Such soft capsules comprise the compound, which may be mixed with water or an oil medium such as peanut oil, liquid paraffin, or olive oil.

Sublingual tablets are designed to dissolve very rapidly. Examples of such compositions include ergotamine tartrate, isosorbide dinitrate, and isoproterenol HCL. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins (such as those commercially available under the trade name EUDRAGIT®), zein, shellac, and polysaccharides.

Powdered and granular compositions of a pharmaceutical preparation of the invention may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions.

Liquid compositions of the pharmaceutical composition of the invention which are suitable for oral administration may be prepared, packaged, and sold either in liquid form or in the form of a dry product intended for reconstitution with water or another suitable vehicle prior to use.

A tablet containing one or more compounds according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents.

Adjuvants or accessory ingredients for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions.

Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compositions according to the present invention may also be administered transdermally, wherein the active agents are incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agents are contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdermal drug delivery may occur through passive diffusion or may be facilitated using electrotransport or iontophoresis.

Compositions for rectal delivery of the compositions of the present invention include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

Topical compositions may be in any form suitable and readily known in the art for delivery of active agents to the body surface, including dermally, buccally, and sublingually. Typical examples of topical compositions include ointments, creams, gels, pastes, and solutions. Compositions for topical administration in the mouth also include lozenges.

In certain embodiments, the compounds and compositions disclosed herein can be delivered via a medical device. Such delivery can generally be via any insertable or implantable medical device, including, but not limited to stents, catheters, balloon catheters, shunts, or coils. In one embodiment, the present invention provides medical devices, such as stents, the surface of which is coated with a compound or composition as described herein. The medical device of this invention can be used, for example, in any application for treating, preventing, or otherwise affecting the course of a disease or condition, such as those disclosed herein.

In another embodiment of the invention, the pharmaceutical composition comprising one or more compounds described herein is administered intermittently. Administration of the therapeutically effective dose may be achieved in a continuous manner, as for example with a sustained-release composition, or it may be achieved according to a desired daily dosage regimen, as for example with one, two, three, or more administrations per day. By "time period of discontinuance" is intended a discontinuing of the continuous sustained-released or daily administration of the composition. The time period of discontinuance may be longer or shorter than the period of continuous sustained-release or daily administration. During the time period of discontinuance, the level of the components of the composition in the relevant tissue is substantially below the maximum level obtained during the treatment. The preferred length of the discontinuance period depends on the concentration of the effective dose and the form of composition used. The discontinuance period can be at least 2 days, at least 4 days or at least 1 week. In other embodiments, the period of discontinuance is at least 1 month, 2 months, 3 months, 4 months or greater. When a sustained-release composition is used, the discontinuance period must be extended to account for the greater residence time of the composition in the body. Alternatively, the frequency of administration of the effective dose of the sustained-release composition can be decreased accordingly. An intermittent schedule of administration of a composition of the invention can continue until the desired therapeutic effect, and ultimately treatment of the disease or disorder, is achieved.

Administration of the composition according to the invention comprises administering a single pharmaceutically active compound as described herein; administering a pharmaceutically active compound as described herein with one or more further pharmaceutically active compounds described herein; or administering one or more pharmaceutically active compounds described herein in combination with one or more further pharmaceutically active compounds (i.e., co-administration). Accordingly, it is recognized that the pharmaceutically active compounds in the compositions of the invention can be administered in a fixed combination (i. e., a single pharmaceutical composition that contains both active materials). Alternatively, the pharmaceutically active compounds may be administered simultaneously (i.e., separate compositions administered at the same time). In another embodiment, the pharmaceutically active compounds are administered sequentially (i. e., administration of one or more pharmaceutically active compounds followed by separate administration or one or more pharmaceutically active compounds). One of skill in the art will recognized that the most preferred method of administration will allow the desired therapeutic effect.

Delivery of a therapeutically effective amount of a composition according to the invention may be obtained via administration of a therapeutically effective dose of the composition. Accordingly, in one embodiment, a therapeutically effective amount is an amount effective to treat abnormal cell proliferation. In another embodiment, a therapeutically effective amount is an amount effective to treat inflammation. In yet another embodiment, a therapeutically effective amount is an amount effective to treat arthritis. In still another embodiment, a therapeutically effective amount is an amount effective to treat asthma.

The active compound is included in the pharmaceutical composition in an amount sufficient to deliver to a patient a therapeutic amount of a compound of the invention in vivo in the absence of serious toxic effects. The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A therapeutically effective amount according to the invention can be determined based on the body weight of the recipient. For example, in one embodiment, a therapeutically effective amount of one or more compounds of the invention is in the range of about 0.1 µg/kg of body weight to about 5 mg/kg of body weight per day. Alternatively, a therapeutically effective amount can be described in terms of a fixed dose. Therefore, in another embodiment, a therapeutically effective amount of one or more compounds of the invention is in the range of about 0.01 mg to about 500 mg per day. Of course, it is understood that such an amount could be divided into a number of smaller dosages administered throughout the day. The effective dosage range of pharmaceutically acceptable salts and prodrugs can be calculated based on the weight of the parent nucleoside to be delivered. If a salt or prodrug exhibits activity in itself, the effective dosage can be estimated as above using the weight of the salt or prodrug, or by other means known to those skilled in the art.

It is contemplated that the compositions of the invention comprising one or more compounds described herein will be administered in therapeutically effective amounts to a mammal, preferably a human. An effective dose of a compound or composition for treatment of any of the conditions or diseases described herein can be readily determined by the use of conventional techniques and by observing results obtained under analogous circumstances. The effective amount of the compositions would be expected to vary according to the weight, sex, age, and medical history of the subject. Of course, other factors could also influence the effective amount of the composition to be delivered, including, but not limited to, the specific disease involved, the degree of involvement or the severity of the disease, the response of the individual patient, the particular compound administered, the mode of administration, the bioavailability characteristics of the preparation administered, the dose regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

V. Active Agent Combinations

In treating various diseases or conditions according to the invention, the compounds disclosed herein may be administered in various combinations. For example, in one embodiment, a composition according to the invention can comprise a single compound described herein. In another embodiment, a composition according to the invention can comprise two or more compounds according to the invention. In still further embodiments, a composition according to the invention can comprise one or more compounds described herein with one or more further compounds known to have therapeutic properties. For example, the compounds described herein can be administered with one or more toxicity-reducing compounds (e.g., folic acid or leucovorin). In further embodiments, the compounds described herein can be administered with one or more compounds known to be an anti-inflammatory, antiarthritic, antibiotic, antifungal, or antiviral agent. Such further compounds can be provided in combination or alternation with the compounds of the invention. In particular embodiments, the compounds of the invention can be provided in combination with one or more compounds selected from the groups described below.

In the foregoing description, certain compounds useful in combination with the compounds of the present invention may be described in reference to specific diseases or conditions commonly treated using the noted compounds. The disclosure of such diseases or conditions is not intended to limit the scope of the invention and particularly does not limit the diseases or conditions that may be treated using the combinations disclosed herein. Rather such exemplary diseases or conditions are provided only to illustrate the types of diseases and conditions typically treated using the additional compounds.

The compounds of the present invention can, in certain embodiments, be used in combination or alternation with antiproliferative agents. Proliferative disorders are currently treated by a variety of classes of compounds including alkylating agents, antimetabolites, natural products, enzymes, biological response modifiers, miscellaneous agents, radiopharmaceuticals (for example, Y-90 tagged to hormones or antibodies), hormones and antagonists. Any of the antiproliferative agents listed below or any other such therapeutic agents and principles as described in, for example, DeVita, V. T., Jr., Hellmann, S., Rosenberg, S. A.; *Cancer: Principles & Practice of Oncology*, 5th ed., Lippincott-Raven Publishers (1997), can be used in combination with the compounds of the present invention Representative, nonlimiting examples of anti-angiogenesis agents suitable for use in combination with the compounds of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs (I-azetidine-2-carboxylic acid (LACA), cis-hydroxyproline), d,1-3,4-dehydroproline, thiaproline, alpha,alpha-dipyridyl, beta-aminopropionitrile fumarate, 4-propyl-5-(4-pyridinyl)-2 (3h)-oxazolone, methotrexate, mitoxantrone, heparin, interferons, 2 macroglobulin-serum, chimp-3, chymostatin, beta-cyclodextrin tetradecasulfate, eponemycin, fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Representative, nonlimiting examples of alkylating agents suitable for use in combination with the compounds of the present invention include, but are not limited to, Nitrogen Mustards, such as Mechlorethamine (Hodgkin's disease, non-Hodgkin's lymphomas), Cyclophosphamide, Ifosfamide (acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas), Melphalan (L-sarcolysin) (multiple myeloma, breast, ovary), Chlorambucil (chronic lymphocytic leukemia, primary macroglobulinemia, Hodgkin's disease, non-Hodgkin's lymphomas), Ethylenimines and Methylmelamines, such as, Hexamethylmelamine (ovary), Thiotepa (bladder, breast, ovary), Alkyl Sulfonates, such as, Busulfan (chronic granulocytic leukemia), Nitrosoureas, such as, Carmustine (BCNU) (Hodgkin's disease, non-Hodgkin's lymphomas, primary brain tumors, multiple myeloma, malignant melanoma), Lomustine (CCNU) (Hodgkin's disease, non-Hodgkin's lymphomas, primary brain tumors, small-cell lung), Semustine (methyl-CCNU) (primary brain tumors, stomach, colon), Streptozocin (STR) (malignant pancreatic insulinoma, malignant carcinoin, Triazenes, such as, Dacarbazine (DTIC-dimethyltriazenoimidazole-carboxamide) (malignant melanoma, Hodgkin's disease, soft-tissue sarcomas).

Representative, nonlimiting examples of anti-metabolite agents suitable for use in combination with the compounds of the present invention include, but are not limited to, Folic Acid Analogs, such as, Methotrexate (amethopterin) (acute lymphocytic leukemia, choriocarcinoma, mycosis fungoides, breast, head and neck, lung, osteogenic sarcoma), Pyrimidine Analogs, such as Fluorouracil (5-fluorouracil-5-FU) Floxuridine (fluorodeoxyuridine-FUdR) (breast, colon, stomach, pancreas, ovary, head and neck, urinary bladder, premalignant skin lesions) (topical), Cytarabine (cytosine arabinoside) (acute granulocytic and acute lymphocytic leukemias), Purine Analogs and Related Inhibitors, such as, Mercaptopurine (6-mercaptopurine-6-MP) (acute lymphocytic, acute granulocytic and chronic granulocytic leukemia), Thioguanine (6-thioguanine-TG) (acute granulocytic, acute lymphocytic and chronic granulocytic leukemia), Pentostatin (2'-deoxycyoformycin) (hairy cell leukemia, mycosis fungoides, chronic lymphocytic leukemia), Vinca Alkaloids, such as, Vinblastine (VLB) (Hodgkin's disease, non-Hodgkin's lymphomas, breast, testis), Vincristine (acute lymphocytic leukemia, neuroblastoma, Wilms' tumor, rhabdomyosarcoma, Hodgkin's disease, non-Hodgkin's lymphomas, small-cell lung), Epipodophylotoxins, such as Etoposide (testis, small-cell lung and other lung, breast, Hodgkin's disease, non-Hodgkin's lymphomas, acute granulocytic leukemia, Kaposi's sarcoma), Teniposide (testis, small-cell lung and other lung, breast, Hodgkin's disease, non-Hodgkin's lymphomas, acute granulocytic leukemia, Kaposi's sarcoma).

Representative, nonlimiting examples of cytotoxic agents suitable for use in combination with the compounds of the present invention include, but are not limited to: doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa -2a recombinant, paclitaxel, teniposide, and streptozoci.

Representative, non-limiting examples of natural products suitable for use in combination with the compounds of the present invention include, but are not limited to: Antibiotics, such as, Dactinomycin (actinonmycin D) (choriocarcinoma, Wilms' tumor rhabdomyosarcoma, testis, Kaposi's sarcoma), Daunorubicin (daunomycin-rubidomycin) (acute granulocytic and acute lymphocytic leukemias), Doxorubicin (soft tissue, osteogenic, and other sarcomas, Hodgkin's disease, non-Hodgkin's lymphomas, acute leukemias, breast, genitourinary thyroid, lung, stomach, neuroblastoma), Bleomycin (testis, head and neck, skin and esophagus lung, and genitourinary tract, Hodgkin's disease, non-Hodgkin's lymphomas), Plicamycin (mithramycin) (testis, malignant hypercalcemia), Mitomycin (mitomycin C) (stomach, cervix, colon, breast, pancreas, bladder, head and neck), Enzymes, such as, L-Asparaginase (acute lymphocytic leukemia), Biological Response Modifiers, such as, Interferon-alpha (hairy cell leukemia, Kaposi's sarcoma, melanoma, carcinoid, renal cell, ovary, bladder, non Hodgkin's lymphomas, mycosis fungoides, multiple myeloma, chronic granulocytic leukemia).

Additional agents that can be used in combination or alternation with the compounds and compositions disclosed herein include, but are not limited to: Platinum Coordination Complexes, such as, Cisplatin (cis-DDP) Carboplatin (testis, ovary, bladder, head and neck, lung, thyroid, cervix, endometrium, neuroblastoma, osteogenic sarcoma); Anthracenedione, such as Mixtozantrone (acute granulocytic leukemia, breast); Substituted Urea, such as, Hydroxyurea (chronic granulocytic leukemia, polycythemia vera, essential thrombocytosis, malignant melanoma); Methylhydrazine Derivatives, such as, Procarbazine (N-methylhydrazine, MIH) (Hodgkin's disease); Adrenocortical Suppressants, such as, Mitotane (o,p'-DDD) (adrenal cortex), Aminoglutethimide (breast); Adrenorticosteriods, such as, Prednisone (acute and chronic lymphocytic leukemias, non-Hodgkin's lymphomas, Hodgkin's disease, breast); Progestins, such as, Hydroxprogesterone caproate, Medroxyprogesterone acetate, Megestrol acetate (endometrium, breast); Steroids, such as, include betamethasone sodium phosphate and betamethasone acetate.

Representative, nonlimiting examples of hormones and antagonists suitable for use in combination with the compounds of the present invention include, but are not limited to, Estrogens: Diethylstibestrol Ethinyl estradiol (breast, prostate); Antiestrogen: Tamoxifen (breast); Androgens: Testosterone propionate Fluxomyesterone (breast); Antiandrogen: Flutamide (prostate); Gonadotropin-Releasing Hormone Analog: Leuprolide (prostate). Other hormones include medroxyprogesterone acetate, estradiol, megestrol acetate, octreotide acetate, diethylstilbestrol diphosphate, testolactone, and goserelin acetate.

The compounds of the present invention can be used in combination or alternation with therapeutic agents used to treat arthritis. Examples of such agents include, but are not limited to, the following:

Nonsteroidal anti-inflammatory drugs (NSAIDs), such as cylcooxygenase-2 (COX-2) inhibitors, aspirin (acetylsalicylic acid), ibuprofen, ketoprofen, and naproxen;

Analgesics, such as acetaminophen, opioid analgesics, and transdermal fentanyl;

Biological response modifiers, such as etanercept, infliximab, adalimumab, anakinra, abatacept, tiruximab, certolizumab pegol, and tocilizumab;

Corticosteroids or steroids, such as glucocorticoids (GC), fluticasone, budesonide, prednisolone, hydrocortisone, adrenaline, Aldosterone, Cortisone Acetate, Desoxymethasone, Dexamethasone, Fluocortolone, Hydrocortisone, Meprednisone, Methylprednisolone, Prednisolone, Prednisone, Prednylidene, Procinonide, Rimexolone, and Suprarenal Cortex;

Disease-modifying antirheumatic drugs (DMARDs), such as hydroxychloroquine, cyclosphosphamide, chlorambucil, the gold compound auranofin, sulfasalazine, minocycline, cyclosporine, toll-like receptor agonists and antagonists, kinase inhibitors (e.g., p38 MAPK) immunosuppressants and tumor necrosis factor (TNF) blockers (e.g., etanercept, infliximab, and adalimumab);

Fibromyalgia medications, such as amitriptyline, fluoxetine, duloxetine, milnacipran, cylobenzaprine, tramadol, gabapentin, pregabalin, and dual-reuptake inhibitors;

Osteoporosis medications, such as estrogens, parathyroid hormones, bisphosphonates, selective receptor molecules, and bone formation agents;

Gout medications, such as allopurinol, probenecid, losartan, and fenofibrate;

Psoriasis medications, such as acitretin; and

Topical treatments, such as topical NSAIDs and capsaicin.

The compounds of the present invention also can be used in combination or alternation with therapeutic agents used to treat asthma. Examples of such agents include, but are not limited to, the following:

Anti-allergics, such as cromolyn sodium and ketotifen fumarate;

Anti-inflammatories, such as NSAIDs and steroidal anti-inflammatories (e.g., beclomethasone dipropionate, budesonide, dexamethasone sodium phosphate, flunisolide, fluticasone propionate, and triamcinolone acetonide);

Anticholinergics, such as ipratropium bromide, belladonna alkaloids, atropine, and oxitropium bromide;

Antihistamines, such as chlorpheniramine, brompheniramine, diphenhydramine, clemastine, dimenhydrinate, cetirizine, hydroxyzine, meclizine, fexofenadine, loratadine, and enadine;

$\beta_2$-adrenergic agonists (beta agonists), such as albutamol, terbutaline, epinephrine, metaproterenol, ipratropium bromide, ephedra (source of alkaloids), ephedrine, and psuedoephedrine;

Leukotriene Receptor Antagonists, such as zafirlukast and zileuton montelukast;

Xanthines (bronchodilators), such as theophylline, dyphylline, and oxtriphylline;

Miscellaneous anti-asthma agents, such as xanthines, methylxanthines, oxitriphylline, aminophylline, phosphodiesterase inhibitors such as zardaverine, calcium antagonists such as nifedipine, and potassium activators such as cromakalim; and Prophylactic agent(s), such as sodium cromoglycate, cromolyn sodium, nedocromil, and ketotifen.

Further, non-limiting examples of active agents that can be used in combination or alternation with the compounds of the present invention include anti-psoriasis agents, anti-Inflammatory Bowel Disease (anti-IBD) agents, anti-chronic obstructive pulmonary disease (anti-COPD) agents, anti-multiple sclerosis agents.

VI. Articles of Manufacture

The present invention also includes an article of manufacture providing a composition comprising one or more compounds described herein. The article of manufacture may contain one or more of the compounds described herein in combination with one or more further therapeutic agents. The article of manufacture can include a vial or other container that contains a composition suitable for use according to the present invention together with any carrier, either dried or in liquid form. In particular, the article of manufacture can comprise a kit including a container with a composition according to the invention. In such a kit, the composition can be delivered in a variety of combinations. For example, the composition can comprise a single dosage comprising all of the active ingredients. Alternately, where more than one active ingredient is provided, the composition can comprise multiple dosages, each comprising one or more active ingredients, the dosages being intended for administration in combination, in succession, or in other close proximity of time. For example, the dosages could be solid forms (e.g., tablets, caplets, capsules, or the like) or liquid forms (e.g., vials), each comprising a single active ingredient, but being provided in blister packs, bags, or the like, for administration in combination.

The article of manufacture further includes instructions for carrying out the method of the invention. Such instructions may be in various forms, such as a label on the container, an insert included in a box in which the container is packaged, or a variety of computer readable formats. The instructions can also be printed on the box in which the vial is packaged. The instructions contain information such as sufficient dosage and administration information so as to allow the subject or a worker in the field to administer the pharmaceutical composition. It is anticipated that a worker in the field encompasses any doctor, nurse, technician, spouse, or other caregiver that might administer the composition. The pharmaceutical composition can also be self-administered by the subject.

VII. Methods of Treatment

As previously noted, antifolates can vary as to the folate-dependant metabolic process inhibited thereby, and many antifolates act on a variety of enzymes. Pemetrexed (also known as ALIMTA® or L-glutamic acid, N-[4-[2-(2-amino-4,7-dihydro-4-oxo-1H-pyrrolo[2,3-d]pyrimidin-5-yl)ethyl]benzoyl-, disodium salt, heptahydrate) is one example of an antifolate known to act on multiple enzymes and has the structure provided in Formula (13). Pemetrexed is known to exhibit antineoplastic activity by inhibiting TS, DHFR, and GARFT.

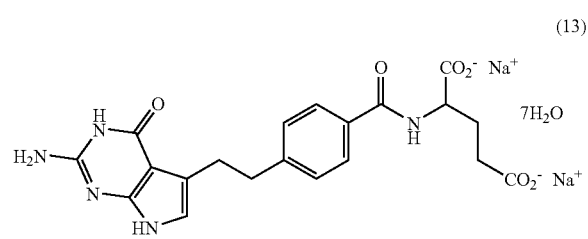

(13)

Thymidylate synthase (TS) is a rate-limiting enzyme in pyrimidine de novo deoxynucleotide biosynthesis and is therefore often a target for chemotherapeutic strategies. In DNA synthesis, TS plays a central role in reductive methylation of deoxyuridine-5'-monophosphate (dUMP) to deoxythymidine-5'-monophosphate (dTMP). Thus, TS inhibition leads directly to depletion of dTMP and subsequently of 2'-deoxythymidine-5'-triphosphate (dTTP), an essential precursor for DNA. This indirectly results in an accumulation of 2'-deoxyuridine-5'-triphosphate (dUTP) and, therefore, leads to so-called "thymine-less death" due to misincorporation of dUTP into DNA and subsequent excision catalyzed by uracil-DNA glycosylase, which causes DNA damage. Both this DNA damage and the noted imbalance in dTTP/dUTP can induce downstream events, leading to apoptosis (cell death).

Dihydrofolate reductase (DHFR) catalyzes the NADPH-dependent reduction of 7,8-dihydrofolate (DHF or H2F) to 5,6,7,8-tetrahydrofolate (THF or H4F). Thus, DHFR is necessary for maintaining intracellular levels of THF, an essential cofactor in the synthetic pathway of purines, thymidylate, and several amino acids.

Glycinamide ribonucleotide formyltransferase (GARFT) is a folate-dependent enzyme in the de novo purine biosynthesis pathway critical to cell division and proliferation. Specifically, GARFT catalyzes the formation of purines from the reaction of 10-formyltetrahydrofolate (10-FTHF) to THF. Inhibition of GARFT results in a depletion in intracellular purine levels, which in turn inhibits DNA and RNA synthesis. Ultimately, disruption of DNA and RNA synthesis by GARFT inhibition results in cell death. The antiproliferative effect associated with GARFT inhibition makes it a particularly desirable target for anti-tumor drugs.

Antifolates, such as pemetrexed, can be transported into cells by mechanisms such as the reduced folate carrier system and the membrane folate binding protein transport system. Once in the cell, pemetrexed is converted to polyglutamylate forms by folyl polyglutamate synthase. The polyglutamylate forms are retained in cells and are inhibitors of TS and GARFT. Polyglutamylation is a time- and concentration-dependent process that occurs in tumor cells and, to a lesser extent, in normal tissues. Polyglutamylated metabolites have an increased intracellular half-life resulting in prolonged drug action in malignant cells.

In many instances, broad action against multiple enzymes may not be desirable. For example, pemetrexed inhibits DHFR, TS, and GARFT. As described above, inhibition of TS and GARFT is strongly related to cell death, thus the desirability of using TS and GARFT inhibitors as anti-tumor drugs. However, the ability of drugs, such as pemetrexed, to induce apoptosis increases the toxicity of the drug (i.e., death of healthy cells as well as tumor cells).

The function of compounds, such as pemetrexed, as inhibitors of TS and GARFT arises from the polyglutamylation of the compound inside the cell. According to the present invention, it has been determined that compounds that are non-polyglutamylatable do not necessarily function as a TS inhibitor or a GARFT inhibitor. However, inhibition of polyglutamylation does not generally affect the ability of a compound to function as a DHFR inhibitor. For example, pemetrexed has been shown to have equivalent DHFR inhibition in comparison to the polyglutamate forms of pemetrexed.

As seen in Formulas (7) through (11), the compounds of the invention comprise a 4-methylidene group in the glutamate moiety of the compounds. Such may also be referred to as a gamma methylene glutamate moiety. The presence of the methylene group makes the inventive compounds non-polyglutamylatable. Accordingly, the compounds of the invention are specific for DHFR inhibition (i.e., do not inhibit TS or GARFT due to the absence of polyglutamylation inside cells). Such specificity is desirable to provide for more specific treatments while avoiding or reducing toxicity and minimizing side-effects more commonly associated with compounds, such as pemetrexed, which act on additional enzymes, such as TS and GARFT.

The compounds of the present invention are particularly useful in the treatment of various conditions wherein disruption of folic acid metabolism is beneficial for treating a symptom of the condition or the condition generally. Accordingly, in further embodiments, the present invention is directed to methods of treating various diseases or conditions. In particular embodiments, the invention provides methods of treating diseases or conditions known or found to be treatable by disruption of folic acid metabolism. In further embodiments, the invention provides methods of treating various diseases or conditions through inhibition of DHFR. In particular embodiments, such inhibition of DHFR is selective. In particular, specific inhibition of DHFR comprises inhibition of DHFR without inhibition of TS or GARFT. In specific embodiments, the invention provides methods of treating conditions, such as abnormal cell proliferation, inflammation (including inflammatory bowel disease), arthritis (particularly rheumatoid arthritis), psoriasis, and asthma.

A. Abnormal Cellular Proliferation

Abnormal cell proliferation has been shown to be the root of many diseases and conditions, including cancer and non-cancer disorders which present a serious health threat. Generally, the growth of the abnormal cells, such as in a tumor, exceeds and is uncoordinated with that of normal cells. Furthermore, the abnormal growth of tumor cells generally persists in an abnormal (i.e., excessive) manner after the cessation of stimuli that originally caused the abnormality in the growth of the cells. A benign tumor is characterized by cells that retain their differentiated features and do not divide in a completely uncontrolled manner. A benign tumor is usually localized and nonmetastatic. A malignant tumor (i.e., cancer) is characterized by cells that are undifferentiated, do not respond to the body's growth control signals, and multiply in an uncontrolled manner. Malignant tumors are invasive and capable of metastasis.

Treatment of diseases or conditions of abnormal cellular proliferation comprises methods of killing, inhibiting, or slowing the growth or increase in size of a body or population of abnormally proliferative cells (including tumors or cancerous growths), reducing the number of cells in the population of abnormally proliferative cells, or preventing the spread of abnormally proliferative cells to other anatomic sites, as well as reducing the size of a growth of abnormally proliferative cells. The term "treatment" does not necessarily mean to imply a cure or a complete abolition of the disorder of abnormal cell proliferation. Prevention of abnormal cellular proliferation comprises methods which slow, delay, control, or decrease the likelihood of the incidence or onset of disorders of abnormal cell proliferation, in comparison to that which would occur in the absence of treatment.

Abnormal cellular proliferation, notably hyperproliferation, can occur as a result of a wide variety of factors, including genetic mutation, infection, exposure to toxins, autoimmune disorders, and benign or malignant tumor induction. Hyperproliferative cell disorders include, but are not limited to, skin disorders, blood vessel disorders, cardiovascular disorders, fibrotic disorders, mesangial disorders, autoimmune disorders, graft-versus-host rejection, tumors, and cancers.

Representative, non-limiting types of non-neoplastic abnormal cellular proliferation disorders that can be treated using the present invention include: skin disorders such as psoriasis, eczema, keratosis, basal cell carcinoma, and squamous cell carcinoma; disorders of the cardiovascular system such as hypertension and vasculo-occlusive diseases (e.g., atherosclerosis, thrombosis and restenosis); blood vessel proliferative disorders such as vasculogenic (formation) and angiogenic (spreading) disorders which result in abnormal proliferation of blood vessels, such as antiogenesis; and disorders associated with the endocrine system such as insulin resistant states including obesity and diabetes mellitus (types 1 & 2).

The compositions and methods of the present invention are also useful for treating inflammatory diseases associated with non-neoplastic abnormal cell proliferation. These include, but are not limited to, inflammatory bowel disease (IBD), rheumatoid arthritis (RA), multiple sclerosis (MS), proliferative glomerulonephritis, lupus erythematosus, scleroderma, temporal arteritis, thromboangiitis obliterans, mucocutaneous lymph node syndrome, asthma, host versus graft, thyroiditis, Grave's disease, antigen-induced airway hyperactivity, pulmonary eosinophilia, Guillain-Barre syndrome, allergic rhinitis, myasthenia gravis, human T-lymphotrophic virus type 1-associated myelopathy, herpes simplex encephalitis, inflammatory myopathies, atherosclerosis, and Goodpasture's syndrome.

In a particular embodiment, the compounds of the present invention are useful in the treatment of psoriasis. Psoriasis is an immune-mediated skin disorder characterized by chronic T-cell stimulation by antigen-presenting cells (APC) occurs in the skin. The various types of psoriasis include, for example, plaque psoriasis (i.e., vulgaris psoriasis), pustular psoriasis, guttate psoriasis, inverse psoriasis, erythrodermic psoriasis, psoriatic arthritis, scalp psoriasis and nail psoriasis. Common systemic treatments for psoriasis include methotrexate, cyclosporin and oral retinoids, but their use is limited by toxicity. Up to 40% of patients with psoriasis also develop psoriatic arthritis (Kormeili T et al. Br J Dermatol. (2004) 151(1):3-15).

In further embodiments, the compounds of the present invention are useful in the treatment of blood vessel proliferative disorders, including vasculogenic (formation) and angiogenic (spreading) disorders which result in abnormal proliferation of blood vessels. Other blood vessel proliferative disorders include arthritis and ocular diseases such as diabetic retinopathy. Abnormal neovascularization is also associated with solid tumors. In a particular embodiment, the compounds of the present invention are useful in the treatment of diseases associated with uncontrolled angiogenesis. Representative, non-limiting diseases of abnormal angiogenesis include rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma, and Oster Webber syndrome. Cancers associated with abnormal blood cell proliferation include hemangioendotheliomas, hemangiomas, and Kaposi's sarcoma.

In further embodiments, the compounds of the present invention are useful in the treatment of disorders of the cardiovascular system involving abnormal cell proliferation. Such disorders include, for example, hypertension, vasculo-occlusive diseases (e.g., atherosclerosis, thrombosis, and restenosis after angioplasty), acute coronary syndromes (such as unstable angina, myocardial infarction, ischemic and non-ischemic cardiomyopathies, post-MI cardiomyopathy, and myocardial fibrosis), and substance-induced cardiomyopathy.

Vascular injury can also result in endothelial and vascular smooth muscle cell proliferation. The injury can be caused by traumatic events or interventions (e.g., angioplasty, vascular graft, anastomosis, organ transplant) (Clowes A et al. A. J. Vasc. Surg (1991) 13:885). Restenosis (e.g., coronary, carotid, and cerebral lesions) is the main complication of successful balloon angioplasty of the coronary arteries. It is believed to be caused by the release of growth factors as a result of mechanical injury to the endothelial cells lining the coronary arteries.

Other atherosclerotic conditions which can be treated or prevented by means of the present invention include diseases of the arterial walls that involve proliferation of endothelial and/or vascular smooth muscle cells, including complications of diabetes, diabetic glomerulosclerosis, and diabetic retinopathy.

In further embodiments, the compounds of the present invention are useful in the treatment of abnormal cell proliferation disorders associated the endocrine system. Such disorders include, for example, insulin resistant states including obesity, diabetes mellitus (types 1 & 2), diabetic retinopathy, macular degeneration associated with diabetes, gestational diabetes, impaired glucose tolerance, polycystic ovarian syndrome, osteoporosis, osteopenia, and accelerated aging of tissues and organs including Werner's syndrome.

In further embodiments, the compounds of the present invention are useful in the treatment of abnormal cell proliferation disorders of the urogenital system. These include, for example, edometriosis, benign prostatic hyperplasia, eiomyoma, polycystic kidney disease, and diabetic nephropathy.

In further embodiments, the compounds of the present invention are useful in the treatment of fibrotic disorders. Medical conditions involving fibrosis include undesirable tissue adhesion resulting from surgery or injury. Non-limiting examples of fibrotic disorders include hepatic cirrhosis and mesangial proliferative cell disorders.

In still further embodiments, abnormal cell proliferation disorders of the tissues and joints can be treated according to the present invention. Such disorders include, for example, Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, and fibromyalgia.

In certain embodiments, abnormal cell proliferation disorders of the pulmonary system can also be treated according to the present invention. These disorders include, for example, asthma, chronic obstructive pulmonary disease (COPD), reactive airway disease, pulmonary fibrosis, and pulmonary hypertension.

Further disorders including an abnormal cellular proliferative component that can be treated according to the invention include Behcet's syndrome, fibrocystic breast disease, fibroadenoma, chronic fatigue syndrome, acute respiratory distress syndrome (ARDS), ischemic heart disease, post-dialysis syndrome, leukemia, acquired immune deficiency syndrome, vasculitis, lipid histiocytosis, septic shock, and familial intestinal polyposes such as Gardner syndrome. Also included in the scope of disorders that may be treated by the compositions and methods of the present invention are virus-induced hyperproliferative diseases including, for example, human papilloma virus-induced disease (e.g., lesions caused by human papilloma virus infection), Epstein-Barr virus-induced disease, scar formation, genital warts, cutaneous warts, and the like.

The compounds of the present invention are further useful in the treatment of conditions and diseases of abnormal cell proliferation including various types of cancers such as primary tumors and tumor metastasis. Specific, non-limiting types of benign tumors that can be treated according to the present invention include hemangiomas, hepatocellular adenoma, cavernous hemangiomas, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, and pyogenic granulomas.

Representative, non-limiting cancers treatable according to the invention include breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

The compounds of the present invention are also useful in preventing or treating proliferative responses associated with organ transplantation which contribute to rejections or other complications. For example, proliferative responses may occur during transplantation of the heart, lung, liver, kidney, and other body organs or organ systems.

B. Inflammation

The compounds of the present invention are also useful in the treatment of diseases characterized by inflammation. Diseases and conditions which have significant inflammatory components are ubiquitous and include, for example, skin disorders, bowel disorders, certain degenerative neurological disorders, arthritis, autoimmune diseases and a variety of other illnesses. Some of these diseases have both an inflammatory and proliferative component, as described above. In particular embodiments the compounds are used to treat inflammatory bowel diseases (IBD), Crohn's disease (CD), ulcerative colitis (UC), chronic obstructive pulmonary disease (COPD), sarcoidosis, or psoriasis. The disclosed compounds are also useful in the treatment of other inflammatory diseases, for example, allergic disorders, skin disorders, transplant rejection, poststreptococcal and autoimmune renal failure, septic shock, systemic inflammatory response syndrome (SIRS), adult respiratory distress syndrome (ARDS), envenomation, lupus erythematosus, Hashimoto's thyroiditis, autoimmune hemolytic anemias, insulin dependent diabetes mellitus, acute rheumatic fever, pelvic inflammatory disease (PID), conjunctivitis, dermatitis, and bronchitis.

Inflammatory bowel diseases (IBD) includes several chronic inflammatory conditions, including Crohn's disease (CD) and ulcerative colitis (UC). Both CD and UC are considered "idiopathic" because their etiology is unknown. While Crohn's disease and ulcerative colitis share many symptoms (e.g., diarrhea, abdominal pain, fever, fatigue), ulcerative colitis is limited to the colon whereas Crohn's disease can involve any segment of the gastrointestinal tract. Both diseases may involve extraintestinal manifestations, including arthritis, diseases of the eye (e.g., episcleritis and iritis), skin diseases (e.g., erythema nodosum and pyoderma gangrenosum), urinary complications, gallstones, and anemia. Strokes, retinal thrombi, and pulmonary emboli are not uncommon, because many patients are in a hypercoagulable state.

In a particular embodiment, the compounds of the present invention, including pharmaceutically acceptable salts, prodrugs and esters thereof, are useful in the treatment of inflammatory bowel disease. In a preferred embodiment, the inflammatory bowel disease is Crohn's disease.

Chronic Obstructive Pulmonary Disease, or COPD, is characterized by a not fully reversible airflow limitation which is progressive and associated with an abnormal inflammatory reaction of the lungs. It is one of the most common respiratory conditions of adults, a major cause of chronic morbidity and mortality, and represents a substantial economic and social burden worldwide (Pauwels R A. Lancet. (2004) 364(9434):613-20). Other names for the disorder include, for example, Chronic Obstructive Airways Disease, (COAD); Chronic Obstructive Lung Disease, (COLD), Chronic Airflow Limitation, (CAL or CAFL) and Chronic Airflow Obstruction (COA).

COPD is characterized by chronic inflammation throughout the airways, parenchyma, and pulmonary vasculature. The inflammation involves a multitude of cells, mediators, and inflammatory effects. Mediators include, for example, mediators include proteases, oxidants and toxic peptides. Over time, inflammation damages the lungs and leads to the pathologic changes characteristic of COPD. Manifestations of disease includes both chronic bronchitis and emphysema. Chronic bronchitis is a long-standing inflammation of the airways that produces a lot of mucus, causing wheezing and infections. It is considered chronic if a subject has coughing and mucus on a regular basis for at least three months a year and for two years in a row. Emphysema is a disease that destroys the alveolae and/or bronchae, causing the air sacs to become enlarged, thus making breathing difficult. Most common in COPD patients is the centrilobular form of emphysema. In a particular embodiment, the compounds of the present invention are useful in the treatment of chronic obstructive pulmonary disease.

Sarcoidosis is yet another chronic inflammatory disease with associated abnormal cell proliferation. Sarcodois is a multisystem granulomatous disorder wherein the granulomas are created by the angiogenic capillary sprouts providing a constant supply of inflammatory cells.

As noted above, inflammation also plays an important role in the pathogenesis of cardiovascular diseases, including restenosis, atherosclerotic complications resulting from plaque rupture, severe tissue ischemia, and heart failure. Inflammatory changes in the arterial wall, for example, are thought to play a major role in the development of restenosis and atherosclerosis (Ross R. N Engl J Med. (1999) 340: 115-126). Local inflammation occurs in the formation the plaques also contributes to the weakening of the fibrous cap of the advanced plaque, ultimately resulting in plaque rupture and acute coronary syndromes (Lind L. Atherosclerosis. (2003) 169(2):203-14).

Multiple sclerosis (MS) is a chronic, often debilitating autoimmune disease that affects the central nervous system. MS is characterized by inflammation which results when the body directs antibodies and white blood cells against proteins in the myelin sheath, fatty material which insulates the nerves in the brain and spinal cord. The result may be multiple areas of scarring (sclerosis), which slows or blocks muscle coordination, visual sensation and other nerve signals. In a particular embodiment, the compounds of the present invention are useful in the treatment of multiple sclerosis.

Inflammatory have been shown to be associated with the pathogenesis of neurological disorders, including Parkinson's disease and Alzheimer's disease (Mirza B. et al. Neuroscience (2000) 95(2):425-32; Gupta A. Int J Clin Pract. (2003) 57(1):36-9; Ghatan E. et al. Neurosci Biobehav Rev. (1999) 23(5):615-33).

The present invention is also useful in the treatment of, for example, allergic disorders, allergic rhinitis, skin disorders, transplant rejection, poststreptococcal and autoimmune renal failure, septic shock, systemic inflammatory response syndrome (SIRS), adult respiratory distress syndrome (ARDS), envenomation, lupus erythematosus, myasthenia gravis, Grave's disease, Hashimoto's thyroiditis, autoimmune hemolytic anemias, insulin dependent diabetes mellitus, glomerulonephritis, and rheumatic fever, pelvic inflammatory disease (PID), conjunctivitis, dermatitis, bronchitis, and rhinitis.

C. Asthma

The compounds disclosed herein can be used in the treatment of asthma. In recent years, it has become clear that the primary underlying pathology of asthma is airway tissue inflammation (Lemanke (2002) *Pediatrics* 109(2):368-372; Nagayama et al. (1995) *Pediatr Allergy Immunol*. 6:204-208). Asthma is associated with a wide range of symptoms and signs, including wheezing, cough, chest tightness, shortness of breath and sputum production. Airway inflammation is a key feature of asthma pathogenesis and its clinical manifestations. Inflammatory cells, including mast cells, eosinophils, and lymphocytes, are present even in the airways of young patients with mild asthma.

Inflammation also plays a role in wheezing disorders, with or without asthma. Asthma is sometimes classified by the triggers that may cause an asthma episode (or asthma attack) or the things that make asthma worse in certain individuals, such as occupational asthma, exercise induced asthma, nocturnal asthma, or steroid resistant asthma. Thus, the compounds of the invention can also be used in the treatment of wheezing disorders, generally.

D. Arthritis and Osteoarthritis

More than 40 million Americans suffer from arthritis in its various forms, including includes over 100 kinds of rheumatic diseases (i.e., diseases affecting joints, muscle, and connective tissue, which makes up or supports various structures of the body, including tendons, cartilage, blood vessels, and internal organs). Representative types of arthritis include rheumatoid (such as soft-tissue rheumatism and non-articular rheumatism), fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout, and systemic lupus erythematosus.

Hypertrophic arthritis or osteoarthritis is the most common form of arthritis and is characterized by the breakdown of the joint's cartilage. Osteoarthritis is common in people over 65, but may appear decades earlier. Breakdown of the cartilage causes bones to rub against each other, causing pain and loss of movement. In recent years, there has been increasing evidence that inflammation plays an important role in osteoarthritis. Nearly one-third of patients ready to undergo joint replacement surgery for osteoarthritis (OA) had severe inflammation in the synovial fluid that surrounds and protects the joints. In one embodiment, the compounds of the present invention are useful in the treatment of osteoarthritis.

The second most common form of arthritis is rheumatoid arthritis. It is an autoimmune disease that can affect the whole body, causing weakness, fatigue, loss of appetite, and muscle pain. Typically, the age of onset is much earlier than osteoarthritis, between ages 20 and 50. Inflammation begins in the synovial lining and can spread to the entire joint. In another embodiment, the compounds of the present invention are useful in the treatment of rheumatoid arthritis.

EXPERIMENTAL

The present invention will now be described with specific reference to various examples. The following examples are not intended to be limiting of the invention and are rather provided as exemplary embodiments.

Example 1

Enzyme Inhibitory Activity of Antifolate Compounds

Novel antifolate compounds according to the invention, herein designated CHL-003 and CHL1007, were prepared for use in various enzyme activity assays. The formulas for CHL-003 and CHL1007 are provided above in Formulas (11) and (12), and methods of synthesis thereof are provided in the Examples below. CHL1007 is the (S) enantiomer of the disodium salt, and CHL-003 is in a racemic form. The activity of CHL-003 and CHL1007 against various enzymes using the enzyme activity assays was evaluated in relation to the known antifolates methotrexate, aminopterin, and Mobiltrex.

The inhibitory potency against DHFR in CCRF-CEM human leukemia cells was assessed by pre-incubating DHFR in the presence of NADPH with five graded concentrations of analog for 3 minutes at 37° C., initiating the reaction by adding DHFR, and quantitating residual DHFR activity. The inhibitor concentration corresponding to 50% relative activity ($IC_{50}$) in nM for the compounds is provided below in Table 1.

TABLE 1

| Compound | $IC_{50}$ (nM) |
| --- | --- |
| Methotrexate | 0.45 |
| Mobiltrex | 1.1 |
| CHL1007 | 5.2 |
| CHL-003 | 12.5 |

The inhibitory potency against TS in CCRF-CEM human T-lymphoblastic leukemia cells was assessed by introducing up to five graded concentrations of compounds into the reaction mixture, initiating the reaction by addition of TS, and quantitating remaining TS activity. The $IC_{50}$ in μM for the compounds is provided below in Table 2.

TABLE 2

| Compound | $IC_{50}$ (μM) |
| --- | --- |
| Methotrexate | 47 |
| Mobiltrex | 8 |
| CHL-003 | >50 |

Two transport systems are responsible for uptake of reduced folates and antifolates in human cells: the reduced folate carrier (RFC) and the folate binding protein (FBP) family. The RFC is the most widely distributed and is generally considered the primary mechanism of transport of reduced folates and antifolates. Since CCRF-CEM cells express only the RFC, the interaction of this carrier with various compounds can be measured by their potency as inhibitors of [$^3$H]MTX influx.

The inhibitory potency of aminopterin, Mobiltrex, and CHL-003 against CCRF-CEM human leukemia cell RFC uptake was assessed by inhibition of uptake by intact cells of 2 μM [$^3$H]MTX (thus aminopterin was evaluated instead of methotrexate). The $IC_{50}$ in $nM^{-1}$ for the compounds is provided below in Table 3.

TABLE 3

| Compound | $IC_{50}$ ($nM^{-1}$) |
| --- | --- |
| Aminopterin | 2.7 |
| Mobiltrex | 2.9 |
| CHL-003 | 1.0 |

The above data illustrates the selectivity of the novel antifolates in enzyme inhibition. As seen in Table 1 through Table 3, CHL-003 exhibits good activity against DHFR ($IC_{50}$ values measured in the nM range) but shows less activity against TS ($IC_{50}$ values measured well into the μM range). Similar tests indicated CHL-003 provided little activity against AICART or GARFT ($IC_{50}$ values >50 μM). As previously noted, such selectivity in activity can be useful for improving activity against specific conditions while avoiding undesirable side effects. The inventive antifolate CHL-003 also exhibited very good activity against RFC uptake, significantly and surprisingly outperforming both aminopterin and Mobiltrex.

Example 2

Synthesis of CHL1007

The compound (S)-N-{4-[2-(2,4-diamino-7H-pyrrolo[2,3-d]pyrimidin-5-yl)ethyl]benzoyl}-4-methylene-L-glutamic acid disodium salt (CHL1007) was synthesized starting from commercial ethyl-4-iodobenzoate and (S)-diethyl-2-amino-4-methylenepentanedionate hydrochloride in eight steps at >99% purity as determined by HPLC.

Step 1

A mixture of ethyl-4-iodobenzoate (180 g, 0.65 mol), allyl alcohol (67 mL, 0.98 mol), $NaHCO_3$ (137 g, 1.63 mol), $Pd(OAc)_2$ (4.39 g, 0.02 mol), and n-$Bu_4NBr$ (210 g, 0.652 mol) in toluene (1.5 L) was stirred at reflux for five hours. The reaction mixture was filtered through CELITE® filter material, rinsed with EtOAc, and the filtrate was washed with water (two washes with 500 mL water each) and a brine salt solution (500 mL). The organic phase was concentrated and the residue was purified by flash chromatography on silica with EtOAc and petroleum ether in a 1:6 ratio. A colorless oil was recovered for use in the next step. The overall reaction scheme for Step 1 is provided below.

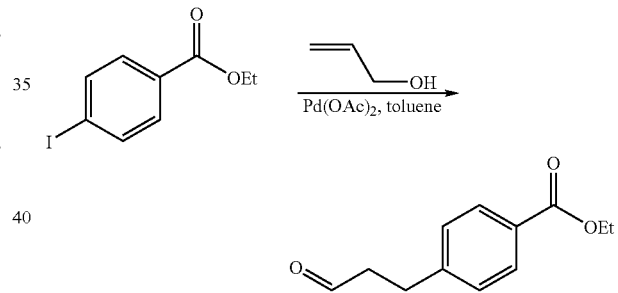

Step 2

The product from Step 1 (193.4 g, 0.94 mol) was combined with para-formaldehyde (28 g, 0.94 mol), N-ethylbenzothiazolium bromide (46 g, 0.19 mol), $Et_3N$ (26 mL, 0.19 mol), and 4 Angstrom molecular sieves in EtOH (1.7 L) and stirred at reflux for 24 hours. The reaction mixture was concentrated and the residue was purified by flash chromatography on silica with EtOAc and petroleum ether in a 1:2 ratio to provide the reaction product. The overall reaction scheme for Step 2 is provided below.

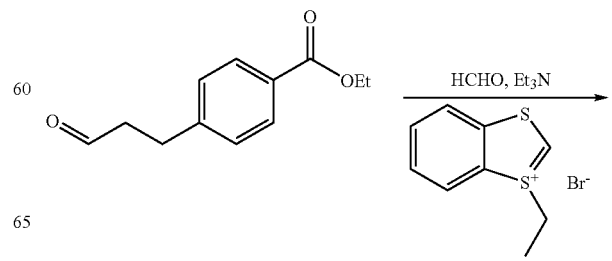

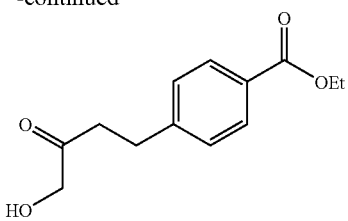

Step 3

A solution of the reaction product from Step 2 (46 g, 0.19 mol) in MeOH (560 mL) was combined with mixture of malonitrile (12.6 g, 0.19 mol) and Et3N (26 mL, 0.19 mol) in MeOH (190 mL), and the resulting solution was stirred at ambient temperature for 24 hours. The solid product was collected by filtration, washed with MeOH, and dried yielding a white solid reaction product. The overall reaction scheme for Step 3 is provided below.

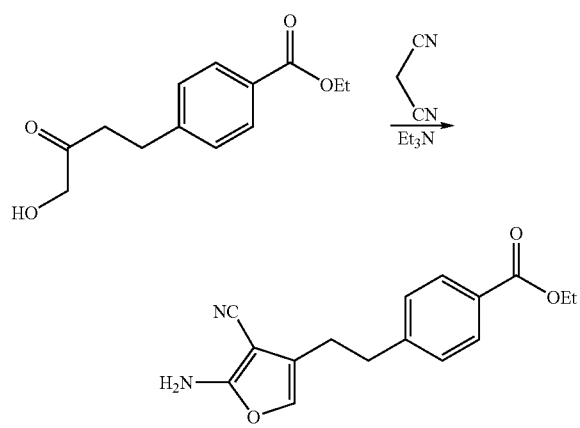

Step 4

The aminonitrile reaction product of Step 3 (20 g, 70 mmol) was added to a solution of guanidine free base (109 mmol, from 10.4 g of guanidine hydrochloride and 7.7 g (109 mmol) of NaOEt) in anhydrous EtOH (600 mL), and the mixture was stirred at reflux for 48 hours. The reaction mixture was concentrated and the residue was purified by flash chromatography on silica with 6% water in acetone as eluent to form the reaction product. The overall reaction scheme for Step 4 is provided below.

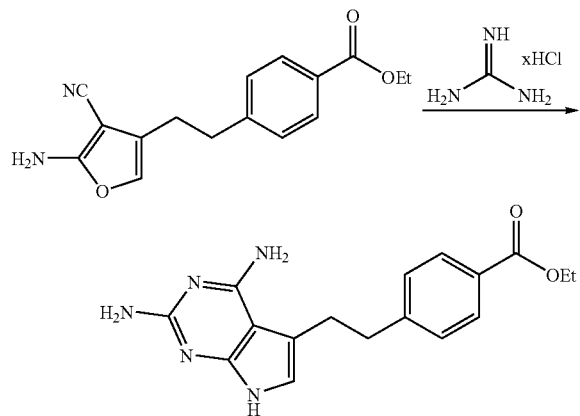

Step 5

A solution of 0.7 g NaOH in 35 mL water was added to a mixture of the reaction product from Step 4 (5.55 g, 17.1 mmol) in MeOH (73 mL), and the mixture was heated under reflux for 2 hours. The reaction mixture was then cooled to ambient temperature, acidified with AcOH (1.2 mL) to form a precipitate to which was added water (100 mL). The precipitate was then filtered, washed with water (150 mL), and dried. The overall reaction scheme for Step 5 is provided below.

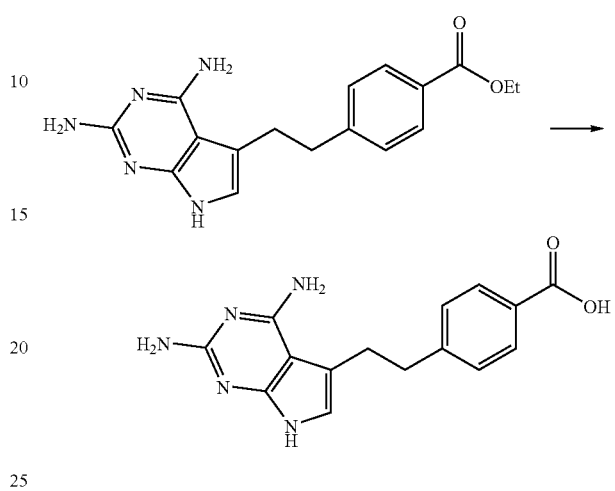

Step 6

HOBt×H2O (1.52 g, 11.2 mmol) and ethylene dichloride (EDC) (2.15 g, 11.2 mmol) were added to a solution of the reaction product from Step 5 (3.34 g, 11.2 mmol) in DMF (70 mL) and left stirring for ten minutes. (S)-diethyl-2-amino-4-methylenepentanedionate×HCl (2.85 g, 11.2 mmol) (enantiomeric purity of 99.8%) and Et3N (3.12 mL, 22.5 mmol) were added, and the reaction mixture was stirred for two hours. After cooling to ambient, the reaction mixture was diluted with water (350 mL) and extracted with dichloromethane. The organic extracts were combined, washed with brine salt solution, dried over Na2SO4, and concentrated. The crude product was recrystallized from toluene, filtered off, washed with Et2O, and dried in vacuum providing the white solid reaction product. The overall reaction scheme for Step 6 is provided below.

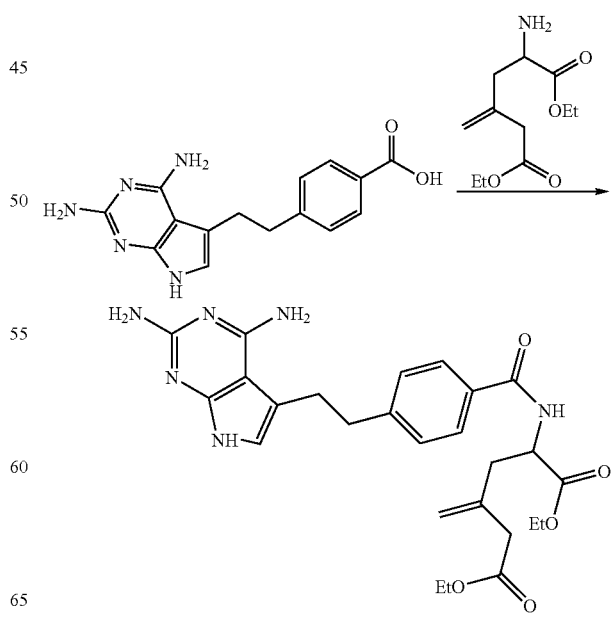

Step 7

To a suspension of the reaction product from Step 6 (3.6 g, 7.28 mmol) in acetonitrile (85 mL) was added 0.25 N NaOH (aq.) (85 mL), and the mixture was stirred for 16 hours. Next, 2 N HCl was added to reach pH 5-6. The formed white precipitate was filtered off, washed with water and acetonitrile, and dried under vacuum to provide a light yellow solid product. The overall reaction scheme for Step 7 is provided below.

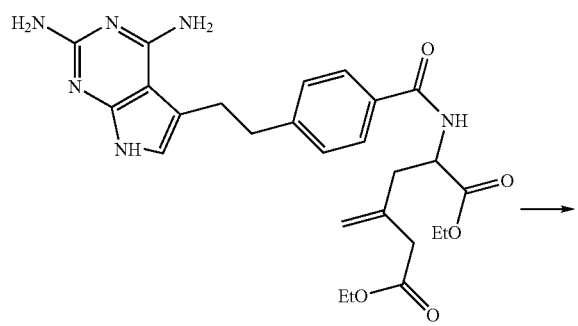

Step 8

A solution of NaOH (0.42 g, 10.5 mmol) in water (20 mL) was added to a suspension of the reaction product from Step 7 (2.29 g, 5.23 mmol) in ethanol (40 mL), and the mixture was stirred for one hour. The reaction mixture was concentrated, acetonitrile (20 mL) was added, and the resulting slurry was stirred overnight. The precipitate was filtered off and dried under vacuum providing 2.45 g (97% yield) of off-white solid reaction product having >99% purity as evaluated by HPLC at 254 nm. The overall reaction scheme for Step 8 is provided below.

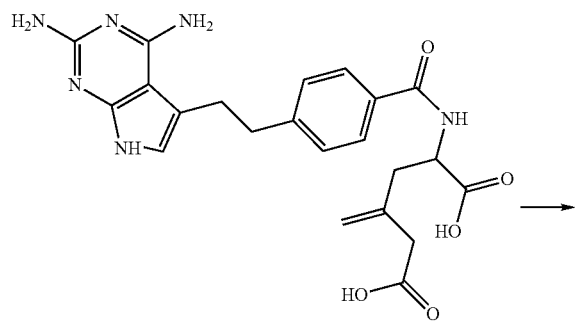

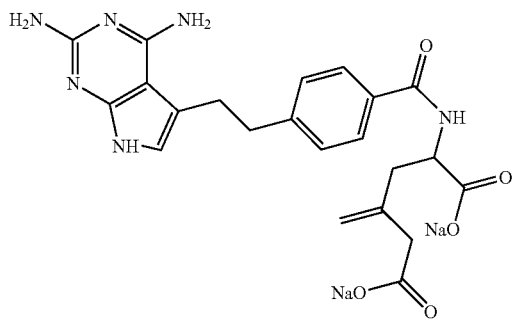

The use of enantiomerically pure (S)-diethyl-2-amino-4-methylenepentanedionate in Step 6 is particularly useful for preparing a final product that is also enantiomerically pure. In the present synthesis, the formed product is enantiomerically pure for the (S) isomer.

Example 3

Synthesis of CHL-003

The compound N-{4-[2-(2,4-diamino-7H-pyrrolo[2,3-d]pyrimidin-5-yl)ethyl]benzoyl}-4-methylene-glutamic acid (CHL-003) was synthesized starting from commercial ethyl-4-iodobenzoate and diethyl-2-amino-4-methylenepentanedionate hydrochloride in eight steps at >99% purity as determined by HPLC. Steps 1-5, 7 and 8 were followed as described in Example 2 above. Step 6, as described below, used the racemic form of diethyl-2-amino-4-methylenepentanedionate×HCl instead of the (S) isomer.

In Step 6, HOBt×H₂O (1.52 g, 11.2 mmol) and EDC (2.15 g, 11.2 mmol) were added to a solution of the reaction product from Step 5 (3.34 g, 11.2 mmol) in DMF (70 mL) and left stirring for ten minutes. Diethyl-2-amino-4-methylenepentanedionate×HCl (2.85 g, 11.2 mmol) and Et₃N (3.12 mL, 22.5 mmol) were added, and the reaction mixture was stirred for two hours. After cooling to ambient, the reaction mixture was diluted with water (350 mL) and extracted with dichloromethane. The organic extracts were combined, washed with brine salt solution, dried over Na₂SO4, and concentrated. The crude product was recrystallized from toluene, filtered off, washed with Et₂O, and dried in vacuum providing the white solid reaction product.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. A compound according to the following formula

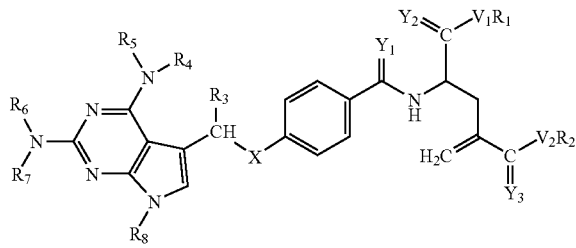

wherein:
X is $CHR_9$ or $NR_9$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;
$R_3$ is H, optionally substituted alkyl, optionally substituted alkenyl, optionally substituted alkynyl, optionally substituted alkoxy, hydroxyl, or halo; and
$R_4$, $R_5$, $R_6$, $R_7$, $R_8$, and $R_9$ independently are H, optionally substituted alkyl, optionally substituted alkenyl, optionally substituted alkynyl, acyl, —C(O)-alkyl, —C(O)-alkenyl, or —C(O)—alkynyl; or
a pharmaceutically acceptable ester, amide, salt or enantiomer thereof.

2. A compound according to claim 1, wherein the compound is in the form of a pharmaceutically acceptable salt.
3. A compound according to claim 2, wherein the compound is in the form of an alkali metal salt.
4. A compound according to claim 3, wherein the compound is in the form of a disodium salt.
5. A compound according to claim 2, wherein one or both of $R_1$ and $R_2$ are replaced by a salt-forming cation.
6. A compound according to claim 5, wherein the salt-forming cation comprises an alkali metal cation.
7. A compound according to claim 2, wherein $V_1$ and $V_2$ are O, and $R_1$ and $R_2$ are both independently replaced by a salt-forming cation.
8. A compound according to claim 7, wherein the salt-forming cation comprises an alkali metal cation.
9. A compound according to claim 1 having the following formula

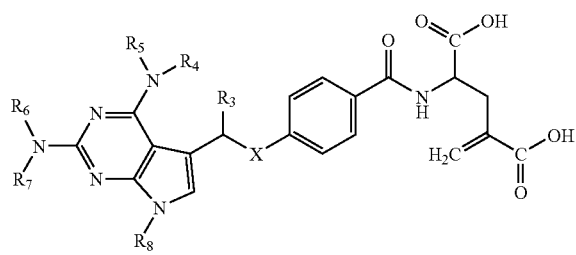

wherein:
X is $CHR_9$ or $NR_9$;
$R_3$ is H, optionally substituted alkyl, optionally substituted alkenyl, optionally substituted alkynyl, optionally substituted alkoxy, hydroxyl, or halo; and
$R_4$, $R_5$, $R_6$, $R_7$, $R_8$, and $R_9$ independently are H, optionally substituted alkyl, optionally substituted alkenyl, optionally substituted alkynyl, acyl, —C(O)-alkyl, —C(O)-alkenyl, or —C(O)—alkynyl; or
a pharmaceutically acceptable ester, amide, salt or enantiomer thereof.

10. A compound according to claim 9, wherein the compound is in the form of a pharmaceutically acceptable salt.
11. A compound according to claim 10, wherein the compound is in the form of an alkali metal salt.
12. A compound according to claim 11, wherein the compound is in the form of a disodium salt.
13. A compound according to claim 1 having the following formula

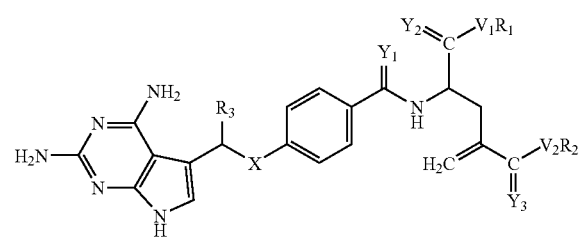

wherein:
X is $CHR_9$ or $NR_9$;
$Y_1$, $Y_2$, and $Y_3$ independently are O or S;
$V_1$ and $V_2$ independently are O, S, or NZ;
Z is H, optionally substituted alkyl, optionally substituted alkenyl, optionally substituted alkynyl, or alkaryl;
$R_1$ and $R_2$ independently are H, optionally substituted alkyl, optionally substituted alkenyl, optionally substituted alkynyl, or alkaryl;
$R_3$ is H, optionally substituted alkyl, optionally substituted alkenyl, optionally substituted alkynyl, optionally substituted alkoxy, hydroxyl, or halo; and
$R_9$ is H, optionally substituted alkyl, optionally substituted alkenyl, optionally substituted alkynyl, acyl, —C(O)-alkyl, —C(O)-alkenyl, or —C(O)-alkynyl; or
a pharmaceutically acceptable ester, amide, salt or enantiomer thereof.

14. A compound according to claim 13, wherein the compound is in the form of a pharmaceutically acceptable salt.
15. A compound according to claim 14, wherein the compound is in the form of an alkali metal salt.
16. A compound according to claim 15, wherein the compound is in the form of a disodium salt.
17. A compound according to claim 14, wherein one or more of $R_1$, $R_2$, and Z are replaced by a salt-forming cation.
18. A compound according to claim 17, wherein the salt-forming cation comprises an alkali metal cation.
19. A compound according to claim 14, wherein $V_1$ and $V_2$ are O, and $R_1$ and $R_2$ are both independently replaced by a salt-forming cation.
20. A compound according to claim 19, wherein the salt-forming cation comprises an alkali metal cation.

21. A compound according to claim 1 having the following formula:

[chemical structure]

or a pharmaceutically acceptable ester, amide, salt or enantiomer thereof.

22. A compound according to claim 21, wherein the compound is in the form of a pharmaceutically acceptable salt.

23. A compound according to claim 22, wherein the compound is in the form of an alkali metal salt.

24. A compound according to claim 22, wherein the compound is in the form of a disodium salt.

25. A compound according to claim 24 having the formula

[chemical structure]

or an enantiomer thereof.

26. A compound according to claim 21, wherein the compound is enantiomerically pure for the (S) enantiomer.

27. A compound according to claim 26, wherein the compound has an enantiomeric purity of at least about 80%.

28. A compound according to claim 26, wherein the compound has an enantiomeric purity of at least about 95%.

29. A compound according to claim 21, wherein the compound is enantiomerically pure for the (R) enantiomer.

30. A compound according to claim 29, wherein the compound has an enantiomeric purity of at least about 80%.

31. A compound according to claim 29, wherein the compound has an enantiomeric purity of at least about 95%.

32. A compound according to claim 25, wherein the compound is enantiomerically pure for the (S) enantiomer.

33. A compound according to claim 32, wherein the compound has an enantiomeric purity of at least about 80%.

34. A compound according to claim 32, wherein the compound has an enantiomeric purity of at least about 95%.

35. A compound according to claim 25, wherein the compound is enantiomerically pure for the (R) enantiomer.

36. A compound according to claim 35, wherein the compound has an enantiomeric purity of at least about 80%.

37. A compound according to claim 35, wherein the compound has an enantiomeric purity of at least about 95%.

38. A pharmaceutical composition comprising a compound according to claim 1 and a pharmaceutically acceptable carrier.

39. A pharmaceutical composition comprising a compound according to claim 9 and a pharmaceutically acceptable carrier.

40. A pharmaceutical composition comprising a compound according to claim 13 and a pharmaceutically acceptable carrier.

41. A pharmaceutical composition comprising a compound according to claim 21 and a pharmaceutically acceptable carrier.

42. A pharmaceutical composition comprising a compound according to claim 25 and a pharmaceutically acceptable carrier.

43. A pharmaceutical composition comprising a compound according to claim 26 and a pharmaceutically acceptable carrier.

44. A pharmaceutical composition comprising a compound according to claim 29 and a pharmaceutically acceptable carrier.

45. A pharmaceutical composition comprising a compound according to claim 32 and a pharmaceutically acceptable carrier.

46. A pharmaceutical composition comprising a compound according to claim 35 and a pharmaceutically acceptable carrier.

\* \* \* \* \*